United States Patent
Evans

(10) Patent No.: US 7,855,078 B2
(45) Date of Patent: Dec. 21, 2010

(54) HIGH RESOLUTION FLOW CYTOMETER

(75) Inventor: Kenneth M. Evans, College Station, TX (US)

(73) Assignee: XY, LLC, Navasota, TX (US)

(*) Notice: Subject to any disclaimer, the term of this patent is extended or adjusted under 35 U.S.C. 154(b) by 978 days.

(21) Appl. No.: 10/524,793

(22) PCT Filed: Aug. 15, 2003

(86) PCT No.: PCT/US03/25812

§ 371 (c)(1),
(2), (4) Date: Oct. 20, 2005

(87) PCT Pub. No.: WO2004/017041

PCT Pub. Date: Feb. 26, 2004

(65) Prior Publication Data

US 2006/0141628 A1 Jun. 29, 2006

Related U.S. Application Data

(60) Provisional application No. 60/404,279, filed on Aug. 15, 2002.

(51) Int. Cl.
*G01N 15/00* (2006.01)
*G01N 19/00* (2006.01)

(52) U.S. Cl. .................. 436/63; 73/865.5; 73/865.8; 324/71.4; 356/440; 356/441; 356/442; 422/73; 436/10; 435/287.1

(58) Field of Classification Search .............. 436/63, 436/10; 73/865.5, 865.8; 324/71.4; 356/440–442; 422/73; 435/287.1

See application file for complete search history.

(56) References Cited

U.S. PATENT DOCUMENTS

| 32,350 | A | 2/1887 | Bhattacharya |
| 3,005,756 | A | 10/1961 | VanDemark et al. |
| 3,299,354 | A | 1/1967 | Hogg |
| 3,499,435 | A | 3/1970 | Rockwell et al. |
| 3,547,526 | A | 12/1970 | Devereux |

(Continued)

FOREIGN PATENT DOCUMENTS

BR 9704313 6/1999

(Continued)

OTHER PUBLICATIONS

Blankenstein, G., Scampavia, L.D., Ruzicka, J., & Christian, G.D. Coaxial Flow Mixer for REal-Time Monitoring of Cellular REsponses in Flow Injection Cytometry(1996). Cytometry 25: 200-204.*

(Continued)

*Primary Examiner*—Krishnan S Menon
*Assistant Examiner*—Rebecca Fritchman
(74) *Attorney, Agent, or Firm*—Craig R. Miles; CR Miles, P.C.

(57) ABSTRACT

High resolution particle differentiation process and separation system that provides enhanced resolution of particles based upon selected particle characteristics. In particular, the system may include an enhanced resolution flow cytometer. In an embodiment, the invention can include at least one fluid source conduit (24) that introduces 0 fluid source stream (24) into an enhanced resolution nozzle (25) at an angle that enhances particle resolution by the cell sensing system (13).

15 Claims, 11 Drawing Sheets

U.S. PATENT DOCUMENTS

| | | |
|---|---|---|
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |

| Patent Number | Date | Inventor(s) |
|---|---|---|
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junnila |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | De Grooth |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | Van den Engh et al. |
| 5,158,889 A | 10/1992 | Hirako et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,204,884 A | 4/1993 | Leary et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,274,240 A | 12/1993 | Mathies et al. |
| 5,275,787 A | 1/1994 | Yuguchi et al. |
| 5,298,967 A | 3/1994 | Wells |
| 5,315,122 A | 5/1994 | Pinsky et al. |
| 5,316,540 A | 5/1994 | McMannis et al. |
| 5,317,162 A | 5/1994 | Pinsky et al. |
| 5,346,990 A | 9/1994 | Spaulding |
| RE34,782 E | 11/1994 | Dandliker et al. |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. |
| 5,395,588 A | 3/1995 | North, Jr. et al. |
| 5,400,179 A | 3/1995 | Ito |
| 5,412,466 A | 5/1995 | Ogino |
| 5,437,987 A | 8/1995 | Ten et al. |
| 5,439,362 A | 8/1995 | Spaulding |
| 5,444,527 A | 8/1995 | Kosaka |
| 5,447,841 A | 9/1995 | Gray et al. |
| 5,447,842 A | 9/1995 | Simons |
| 5,452,054 A | 9/1995 | Dewa et al. |
| 5,457,526 A | 10/1995 | Kosaka |
| 5,461,145 A | 10/1995 | Kudo et al. |
| 5,464,581 A | 11/1995 | Van den Engh |
| 5,466,572 A | 11/1995 | Sasaki et al. |
| 5,467,189 A | 11/1995 | Kreikebaum et al. |
| 5,469,375 A | 11/1995 | Kosaka |
| 5,471,294 A | 11/1995 | Ogino |
| 5,471,299 A | 11/1995 | Kaye et al. |
| 5,475,487 A | 12/1995 | Mariella, Jr. et al. |
| 5,480,774 A | 1/1996 | Hew et al. |
| 5,480,775 A | 1/1996 | Ito et al. |
| 5,483,469 A | 1/1996 | Van den Engh et al. |
| 5,488,469 A | 1/1996 | Yamamoto et al. |
| 5,492,534 A | 2/1996 | Atheyde |
| 5,494,795 A | 2/1996 | Guerry et al. |
| 5,495,719 A | 3/1996 | Gray, Jr. |
| 5,496,272 A | 3/1996 | Chung et al. |
| 5,503,994 A | 4/1996 | Shear et al. |
| 5,514,537 A | 5/1996 | Chandler |
| 5,523,573 A | 6/1996 | Hanninen et al. |
| 5,532,155 A | 7/1996 | Ranoux |
| 5,547,849 A | 8/1996 | Baer et al. |
| 5,548,395 A | 8/1996 | Kosaka |
| 5,548,661 A | 8/1996 | Price et al. |
| 5,550,058 A | 8/1996 | Corio et al. |
| 5,556,764 A | 9/1996 | Sizto et al. |
| 5,558,998 A | 9/1996 | Hammond et al. |
| 5,559,032 A | 9/1996 | Pomeroy et al. |
| 5,578,449 A | 11/1996 | Frasch et al. |
| 5,579,159 A | 11/1996 | Ito |
| 5,584,982 A | 12/1996 | Dovichi et al. |
| 5,589,457 A | 12/1996 | Wiltbank |
| 5,596,401 A | 1/1997 | Kusuzawa |
| 5,601,234 A | 2/1997 | Larue |
| 5,601,235 A | 2/1997 | Booker et al. |
| 5,601,533 A | 2/1997 | Hancke et al. |
| 5,602,039 A | 2/1997 | Van den Engh |
| 5,602,349 A | 2/1997 | Van den Engh |
| 5,608,519 A | 3/1997 | Grouley et al. |
| 5,620,842 A | 4/1997 | Davis et al. |
| 5,622,820 A | 4/1997 | Rossi |
| 5,627,037 A | 5/1997 | Ward et al. |
| 5,633,503 A | 5/1997 | Kosaka |
| 5,641,457 A | 6/1997 | Vardanega |
| 5,643,796 A | 7/1997 | Van Den Engh et al. |
| 5,650,847 A | 7/1997 | Maltsev et al. |
| 5,658,751 A | 8/1997 | Yue et al. |
| 5,660,997 A | 8/1997 | Spaulding |
| 5,663,048 A | 9/1997 | Winkfein et al. |
| 5,665,315 A | 9/1997 | Robert et al. |
| 5,672,880 A | 9/1997 | Kain |
| 5,674,743 A | 10/1997 | Ulmer |
| 5,675,401 A | 10/1997 | Wangler et al. |
| 5,682,038 A | 10/1997 | Hoffman |
| 5,684,575 A | 11/1997 | Steen |
| 5,687,727 A | 11/1997 | Kraus et al. |
| 5,690,815 A | 11/1997 | Krasnoff et al. |
| 5,690,895 A | 11/1997 | Matsumoto et al. |
| 5,691,133 A | 11/1997 | Critser et al. |
| 5,693,534 A | 12/1997 | Alak et al. |
| 5,696,157 A | 12/1997 | Wang et al. |
| 5,700,692 A | 12/1997 | Sweet |
| 5,701,012 A | 12/1997 | Ho |
| 5,707,808 A | 1/1998 | Roslaniec et al. |
| 5,708,868 A | 1/1998 | Ishikawa |
| 5,712,807 A | 1/1998 | Bangham |
| 5,719,666 A | 2/1998 | Fukuda et al. |
| 5,719,667 A | 2/1998 | Miers |
| 5,726,009 A | 3/1998 | Connors et al. |
| 5,726,364 A | 3/1998 | Van den Engh |

| Patent | Date | Inventor |
|---|---|---|
| 5,726,751 A | 3/1998 | Altendorf et al. |
| 5,730,941 A | 3/1998 | Lefevre et al. |
| 5,736,330 A | 4/1998 | Fulton |
| 5,739,902 A | 4/1998 | Gjelsnes et al. |
| 5,745,308 A | 4/1998 | Spangenberg |
| 5,747,349 A | 5/1998 | Van den Engh et al. |
| 5,759,767 A | 6/1998 | Lakowicz et al. |
| 5,777,732 A | 7/1998 | Hanninen et al. |
| 5,780,230 A | 7/1998 | Li et al. |
| 5,786,560 A | 7/1998 | Tatah et al. |
| 5,790,692 A | 8/1998 | Price et al. |
| 5,793,485 A | 8/1998 | Gourley |
| 5,796,112 A | 8/1998 | Ichie |
| 5,798,276 A | 8/1998 | Haugland et al. |
| 5,799,830 A | 9/1998 | Carroll et al. |
| 5,804,436 A | 9/1998 | Okun et al. |
| 5,815,262 A | 9/1998 | Schrof et al. |
| 5,819,948 A | 10/1998 | Van den Engh |
| 5,824,269 A | 10/1998 | Kosaka et al. |
| 5,831,723 A | 11/1998 | Kubota et al. |
| 5,835,262 A | 11/1998 | Iketaki et al. |
| 5,840,504 A | 11/1998 | Blecher |
| 5,844,685 A | 12/1998 | Gontin |
| 5,846,737 A | 12/1998 | Kang |
| 5,866,344 A | 2/1999 | Georgiou |
| 5,868,767 A | 2/1999 | Farley et al. |
| 5,872,627 A | 2/1999 | Miers |
| 5,873,254 A | 2/1999 | Arav |
| 5,874,266 A | 2/1999 | Paisson |
| 5,876,942 A | 3/1999 | Cheng et al. |
| 5,880,457 A | 3/1999 | Tomiyama et al. |
| 5,880,474 A | 3/1999 | Norton et al. |
| 5,883,378 A | 3/1999 | Irish et al. |
| 5,888,730 A | 3/1999 | Gray et al. |
| 5,891,734 A | 4/1999 | Gill et al. |
| 5,893,843 A | 4/1999 | Rodrigues Claro |
| 5,895,764 A | 4/1999 | Sklar et al. |
| 5,895,922 A | 4/1999 | Ho |
| 5,899,848 A | 5/1999 | Haubrich |
| 5,909,278 A | 6/1999 | Deka et al. |
| 5,912,257 A | 6/1999 | Prasad et al. |
| 5,916,144 A | 6/1999 | Prather et al. |
| 5,916,449 A | 6/1999 | Ellwart et al. |
| 5,917,733 A | 6/1999 | Bangham |
| 5,919,360 A | 7/1999 | Contaxis, III et al. |
| 5,919,621 A | 7/1999 | Brown |
| 5,934,885 A | 8/1999 | Farrell et al. |
| 5,962,238 A | 10/1999 | Sizto et al. |
| 5,972,710 A | 10/1999 | Weigl et al. |
| 5,973,842 A | 10/1999 | Spangenberg |
| 5,985,216 A | 11/1999 | Rens et al. |
| 5,985,538 A | 11/1999 | Stachecju |
| 5,990,479 A | 11/1999 | Weiss et al. |
| 5,991,028 A | 11/1999 | Cabib et al. |
| 5,998,140 A | 12/1999 | Dervan et al. |
| 5,998,212 A | 12/1999 | Corio et al. |
| 6,002,471 A | 12/1999 | Quake |
| 6,003,678 A | 12/1999 | den Engh |
| 6,042,249 A | 3/2000 | Spangenberg |
| 6,050,935 A | 4/2000 | Ranoux et al. |
| 6,071,689 A | 6/2000 | Seidel et al. |
| 6,079,836 A | 6/2000 | Burr et al. |
| 6,086,574 A | 7/2000 | Carroll et al. |
| 6,087,352 A | 7/2000 | Trout |
| 6,090,947 A | 7/2000 | Dervan et al. |
| 6,097,485 A | 8/2000 | Lievan |
| 6,111,398 A | 8/2000 | Graham |
| 6,117,068 A | 9/2000 | Gourley et al. |
| 6,119,465 A | 9/2000 | Mullens et al. |
| 6,120,735 A | 9/2000 | Zborowski et al. |
| 6,128,133 A | 10/2000 | Bergmann |
| 6,130,034 A | 10/2000 | Aitken |
| 6,132,961 A | 10/2000 | Gray et al. |
| 6,133,044 A | 10/2000 | Van den Engh |
| 6,133,995 A | 10/2000 | Kubota |
| 6,139,800 A | 10/2000 | Chandler |
| 6,140,121 A | 10/2000 | Ellington et al. |
| 6,143,535 A | 11/2000 | Paisson |
| 6,143,901 A | 11/2000 | Dervan |
| 6,146,837 A | 11/2000 | van de Winkel |
| 6,149,867 A | 11/2000 | Seidel et al. |
| 6,153,373 A | 11/2000 | Benjamin et al. |
| 6,154,276 A | 11/2000 | Mariella, Jr. |
| 6,175,409 B1 | 1/2001 | Nielsen et al. |
| 6,177,277 B1 | 1/2001 | Soini |
| 6,193,647 B1 | 2/2001 | Beebe et al. |
| 6,201,628 B1 | 3/2001 | Basiji et al. |
| 6,207,392 B1 | 3/2001 | Weiss et al. |
| 6,208,411 B1 | 3/2001 | Vaez-Iravani |
| 6,211,477 B1 | 4/2001 | Cardott et al. |
| 6,214,560 B1 | 4/2001 | Yguerabide et al. |
| 6,221,654 B1 | 4/2001 | Quake et al. |
| 6,221,671 B1 | 4/2001 | Groner et al. |
| 6,230,982 B1 * | 5/2001 | Newton ............ 239/10 |
| 6,238,920 B1 | 5/2001 | Nagai et al. |
| 6,247,323 B1 | 6/2001 | Maeda |
| 6,248,590 B1 | 6/2001 | Malachowski |
| 6,256,096 B1 | 7/2001 | Johnson |
| 6,263,745 B1 | 7/2001 | Buchanan et al. |
| 6,283,920 B1 | 9/2001 | Eberle et al. |
| 6,296,810 B1 | 10/2001 | Ulmer |
| 6,309,815 B1 | 10/2001 | Tash et al. |
| 6,316,234 B1 | 11/2001 | Bova |
| 6,317,511 B1 | 11/2001 | Horiuchi |
| 6,322,901 B1 | 11/2001 | Bawendi et al. |
| 6,323,632 B1 | 11/2001 | Husher et al. |
| 6,326,144 B1 | 12/2001 | Bawendi et al. |
| 6,328,071 B1 | 12/2001 | Austin |
| 6,329,158 B1 | 12/2001 | Hoffman et al. |
| 6,332,540 B1 | 12/2001 | Paul et al. |
| 6,357,307 B2 | 3/2002 | Buchanan et al. |
| 6,368,786 B1 | 4/2002 | Saint-Ramon et al. |
| 6,372,422 B1 | 4/2002 | Seidel et al. |
| 6,372,506 B1 | 4/2002 | Norton |
| 6,384,951 B1 | 5/2002 | Basiji et al. |
| 6,395,305 B1 | 5/2002 | Buhr et al. |
| 6,400,453 B1 | 6/2002 | Hansen |
| 6,411,835 B1 | 6/2002 | Modell et al. |
| 6,411,904 B1 | 6/2002 | Chandler |
| 6,416,190 B1 | 7/2002 | Grier et al. |
| 6,423,505 B1 | 7/2002 | Davis |
| 6,423,551 B1 | 7/2002 | Weiss et al. |
| 6,432,630 B1 | 8/2002 | Blankenstein |
| 6,432,638 B2 | 8/2002 | Dervan et al. |
| 6,452,372 B1 | 9/2002 | Husher et al. |
| 6,454,945 B1 | 9/2002 | Weigl et al. |
| 6,456,055 B2 | 9/2002 | Shinabe et al. |
| 6,463,314 B1 | 10/2002 | Haruna |
| 6,465,169 B2 | 10/2002 | Walderich et al. |
| 6,473,176 B2 | 10/2002 | Basiji et al. |
| 6,482,652 B2 | 11/2002 | Furlong et al. |
| 6,489,092 B1 | 12/2002 | Benjamin et al. |
| 6,495,333 B1 | 12/2002 | Willmann et al. |
| 6,495,366 B1 | 12/2002 | Briggs |
| 6,503,698 B1 | 1/2003 | Dobrinsky et al. |
| 6,511,853 B1 | 1/2003 | Kopf-Sill et al. |
| 6,514,722 B2 | 2/2003 | Paisson et al. |
| 6,524,860 B1 | 2/2003 | Seidel et al. |
| 6,528,802 B1 | 3/2003 | Koenig et al. |
| 6,534,308 B1 | 3/2003 | Palsson et al. |
| 6,537,829 B1 | 3/2003 | Zarling et al. |
| 6,540,895 B1 | 4/2003 | Spence et al. |
| 6,563,583 B2 | 5/2003 | Ortyn et al. |
| 6,576,291 B2 | 6/2003 | Bawendi et al. |
| 6,577,387 B2 | 6/2003 | Ross, III et al. |
| 6,580,504 B1 | 6/2003 | Ortyn et al. |

| | | |
|---|---|---|
| 6,587,203 B2 | 7/2003 | Colon |
| 6,589,792 B1 | 7/2003 | Malachowski |
| 6,590,911 B1 | 7/2003 | Spinelli et al. |
| 6,596,143 B1 | 7/2003 | Wang et al. |
| 6,596,499 B2 | 7/2003 | Jalink |
| 6,604,435 B2 * | 8/2003 | Buchanan et al. .......... 73/865.5 |
| 6,613,525 B2 | 9/2003 | Nelson et al. |
| 6,617,107 B1 | 9/2003 | Dean |
| 6,618,143 B2 | 9/2003 | Roche et al. |
| 6,618,679 B2 | 9/2003 | Loehrlein et al. |
| 6,641,708 B1 | 11/2003 | Becker et al. |
| 6,642,018 B1 | 11/2003 | Koller et al. |
| 6,658,357 B2 | 12/2003 | Chandler |
| 6,664,550 B2 | 12/2003 | Rader et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,674,525 B2 | 1/2004 | Bardell et al. |
| 6,698,627 B2 | 3/2004 | Garcia et al. |
| 6,700,130 B2 | 3/2004 | Fritz |
| 6,703,621 B2 | 3/2004 | Wolleschensky |
| 6,704,313 B1 | 3/2004 | De Resende et al. |
| 6,706,163 B2 | 3/2004 | Seul et al. |
| 6,707,555 B1 | 3/2004 | Kusuzawa et al. |
| 6,713,019 B2 | 3/2004 | Ozasa et al. |
| 6,729,369 B2 | 5/2004 | Neas et al. |
| 6,746,873 B1 | 6/2004 | Buchanan et al. |
| 6,752,298 B2 | 6/2004 | Garcia et al. |
| 6,753,161 B2 | 6/2004 | Koller et al. |
| 6,761,286 B2 | 7/2004 | Py et al. |
| 6,761,288 B2 | 7/2004 | Garcia |
| 6,767,706 B2 | 7/2004 | Quake |
| 6,780,377 B2 | 8/2004 | Hall et al. |
| 6,782,768 B2 | 8/2004 | Buchanan et al. |
| 6,789,706 B2 | 9/2004 | Abergel et al. |
| 6,789,750 B1 | 9/2004 | Heldt |
| 6,793,387 B2 | 9/2004 | Neas et al. |
| 6,813,017 B1 | 11/2004 | Hoffman et al. |
| 6,819,411 B1 | 11/2004 | Sharpe et al. |
| 6,849,394 B2 | 2/2005 | Rozeboom et al. |
| 6,849,423 B2 | 2/2005 | Mutz et al. |
| 6,861,265 B1 | 3/2005 | Van den Engh |
| 6,941,005 B2 | 9/2005 | Lary et al. |
| 7,015,310 B2 | 3/2006 | Remington et al. |
| 7,094,527 B2 | 8/2006 | Seidel et al. |
| 7,105,355 B2 | 9/2006 | Kurabayashi et al. |
| 7,195,920 B2 | 3/2007 | Seidel et al. |
| 7,208,265 B1 | 4/2007 | Schenk |
| 7,221,453 B2 | 5/2007 | Sharpe et al. |
| 2001/0006416 A1 | 7/2001 | Johnson |
| 2002/0047697 A1 | 4/2002 | Husher et al. |
| 2002/0058332 A1 | 5/2002 | Quake et al. |
| 2002/0064809 A1 | 5/2002 | Mutz et al. |
| 2002/0096123 A1 | 7/2002 | Whittier et al. |
| 2002/0113965 A1 | 8/2002 | Roche et al. |
| 2002/0115055 A1 | 8/2002 | Matta |
| 2002/0119558 A1 | 8/2002 | Seidel et al. |
| 2002/0131957 A1 | 9/2002 | Gavin |
| 2002/0141902 A1 | 10/2002 | Ozasa et al. |
| 2002/0171827 A1 | 11/2002 | Van den Engh |
| 2002/0182590 A1 | 12/2002 | Strange et al. |
| 2002/0186375 A1 | 12/2002 | Asbury et al. |
| 2002/0186874 A1 | 12/2002 | Price et al. |
| 2002/0198928 A1 | 12/2002 | Bukshpan et al. |
| 2003/0048433 A1 | 3/2003 | Desjonqueres |
| 2003/0059764 A1 | 3/2003 | Ravkin et al. |
| 2003/0059945 A1 | 3/2003 | Dzekunov et al. |
| 2003/0078703 A1 | 4/2003 | Potts |
| 2003/0096405 A1 | 5/2003 | Takayama et al. |
| 2003/0098421 A1 | 5/2003 | Ho |
| 2003/0113765 A1 | 6/2003 | Dempcy et al. |
| 2003/0119050 A1 | 6/2003 | Shai |
| 2003/0119206 A1 | 6/2003 | Shai |
| 2003/0129091 A1 | 7/2003 | Seidel et al. |
| 2003/0157475 A1 | 8/2003 | Schenk |
| 2003/0165812 A1 | 9/2003 | Takayama et al. |
| 2003/0175917 A1 | 9/2003 | Cumming |
| 2003/0175980 A1 | 9/2003 | Hayenga et al. |
| 2003/0190681 A1 | 10/2003 | Shai |
| 2003/0207461 A1 | 11/2003 | Bell et al. |
| 2003/0209059 A1 | 11/2003 | Kawano |
| 2004/0005582 A1 | 1/2004 | Shipwast |
| 2004/0031071 A1 | 2/2004 | Morris et al. |
| 2004/0034879 A1 | 2/2004 | Rothstein et al. |
| 2004/0049801 A1 | 3/2004 | Seidel |
| 2004/0053243 A1 | 3/2004 | Evans |
| 2004/0055030 A1 | 3/2004 | Maxwell et al. |
| 2004/0061070 A1 | 4/2004 | Hansen |
| 2004/0061853 A1 | 4/2004 | Blasenheim |
| 2004/0062685 A1 | 4/2004 | Norton et al. |
| 2004/0107150 A1 | 6/2004 | Neas et al. |
| 2004/0132001 A1 | 7/2004 | Seidel et al. |
| 2005/0003472 A1 | 1/2005 | Anzar |
| 2005/0011582 A1 | 1/2005 | Haug |
| 2005/0064383 A1 | 3/2005 | Bashkin et al. |
| 2005/0112541 A1 | 5/2005 | Durack |
| 2005/0214733 A1 | 9/2005 | Graham |
| 2005/0244805 A1 | 11/2005 | Ludwig et al. |
| 2005/0282245 A1 | 12/2005 | Ludwig et al. |
| 2006/0118167 A1 | 6/2006 | Neas et al. |
| 2006/0147894 A1 | 7/2006 | Sowter |
| 2006/0263829 A1 | 11/2006 | Evans et al. |
| 2006/0281176 A1 | 12/2006 | Seidel et al. |
| 2007/0026379 A1 | 2/2007 | Seidel et al. |
| 2007/0042342 A1 | 2/2007 | Seidel et al. |
| 2007/0092860 A1 | 4/2007 | Schenk |
| 2007/0099171 A1 | 5/2007 | Schenk |
| 2007/0099260 A1 | 5/2007 | Seidel et al. |
| 2007/0117086 A1 | 5/2007 | Evans et al. |

FOREIGN PATENT DOCUMENTS

| | | |
|---|---|---|
| CA | 1029833 | 4/1978 |
| CA | 1 250 808 | 3/1989 |
| CA | 2113957 A1 | 1/1994 |
| CN | ZL 03109426.0 | 12/2005 |
| DE | 69028526 | 2/1997 |
| DE | 195 49 015 C1 | 4/1997 |
| DE | 198 82 943.3 | 2/2001 |
| EP | 0025296 A2 | 3/1981 |
| EP | 0 046 345 A2 | 2/1982 |
| EP | 0 068 404 B1 | 1/1983 |
| EP | 0071538 A1 | 2/1983 |
| EP | 0 026 770 B1 | 3/1983 |
| EP | 0 029 662 B1 | 2/1984 |
| EP | 0 025 296 B1 | 5/1985 |
| EP | 0140616 | 5/1985 |
| EP | 0 158 147 A2 | 10/1985 |
| EP | 0160201 A2 | 11/1985 |
| EP | 0189702 A1 | 8/1986 |
| EP | 0 229 814 B1 | 7/1987 |
| EP | 0 246 604 A2 | 11/1987 |
| EP | 0288029 B1 | 4/1988 |
| EP | 0276166 A2 | 7/1988 |
| EP | 0 289 677 A2 | 11/1988 |
| EP | 0 316 173 A1 | 5/1989 |
| EP | 0 317 809 A2 | 5/1989 |
| EP | A-0 366794 | 5/1990 |
| EP | 0 409 293 A2 | 1/1991 |
| EP | 0461618 | 12/1991 |
| EP | 0 463 562 A1 | 1/1992 |
| EP | 0468100 A1 | 1/1992 |
| EP | 0474 187 A2 | 3/1992 |
| EP | 0 316 172 B1 | 7/1992 |
| EP | 0 316 171 B1 | 9/1992 |
| EP | 0570102 A1 | 3/1993 |

| | | | | | | |
|---|---|---|---|---|---|---|
| EP | 0538786 A | 4/1993 | | WO | WO 89/04472 A1 | 5/1989 |
| EP | 0 279 000 B1 | 7/1993 | | WO | WO 90/13315 A1 | 11/1990 |
| EP | 0 553 951 A1 | 8/1993 | | WO | WO 9105236 | 4/1991 |
| EP | 0 288 029 B1 | 1/1994 | | WO | WO 92/08120 A1 | 5/1992 |
| EP | 0 381 694 B1 | 6/1994 | | WO | WO 92/17288 A1 | 10/1992 |
| EP | 0 361 504 B1 | 7/1994 | | WO | WO 93/10803 | 6/1993 |
| EP | 606847 A2 | 7/1994 | | WO | 9317322 A1 | 9/1993 |
| EP | 0 289 200 B2 | 8/1994 | | WO | WO 94/22001 A1 | 9/1994 |
| EP | 0 555 212 B1 | 10/1994 | | WO | WO 96/04542 A1 | 2/1996 |
| EP | 0 361 503 B1 | 11/1994 | | WO | WO 96/12171 | 4/1996 |
| EP | 0 696 731 A2 | 2/1996 | | WO | WO 96/12172 | 4/1996 |
| EP | 0 705 978 A2 | 4/1996 | | WO | WO 96/12173 A1 | 4/1996 |
| EP | 0 711 991 A1 | 5/1996 | | WO | WO 96/31764 | 10/1996 |
| EP | 0 471 758 B1 | 9/1996 | | WO | WO 96/33806 A1 | 10/1996 |
| EP | 0 736 765 A1 | 10/1996 | | WO | WO 97/29354 A1 | 8/1997 |
| EP | 0 545 284 B1 | 2/1997 | | WO | WO 97/30338 A1 | 8/1997 |
| EP | 0 360 487 B1 | 7/1997 | | WO | WO 97/35189 A1 | 9/1997 |
| EP | 0 412 431 B1 | 10/1997 | | WO | WO 97/43620 A1 | 11/1997 |
| EP | 0 526 131 B1 | 1/1998 | | WO | WO 98/34094 | 8/1998 |
| EP | A-0 478155 | 1/1998 | | WO | WO 98/48259 | 10/1998 |
| EP | 0 822 404 A3 | 2/1998 | | WO | WO 98/57152 A1 | 12/1998 |
| EP | 0 822 401 A2 | 4/1998 | | WO | WO 99/05504 | 2/1999 |
| EP | 0781985 A3 | 7/1998 | | WO | WO 99/33956 | 7/1999 |
| EP | 0 556 748 B1 | 10/1998 | | WO | WO 99/38883 | 8/1999 |
| EP | 0 430 402 B1 | 1/1999 | | WO | WO 99/42810 | 8/1999 |
| EP | 0 529 666 B1 | 4/2000 | | WO | WO 99/44035 | 9/1999 |
| EP | 0 994 342 A3 | 4/2000 | | WO | WO 99/44037 A1 | 9/1999 |
| EP | 0 752 133 81 | 6/2000 | | WO | WO 99/47906 A1 | 9/1999 |
| EP | 1 018 644 A2 | 7/2000 | | WO | WO 99/60397 A1 | 11/1999 |
| EP | 1 118 268 A1 | 7/2001 | | WO | WO 9957955 | 11/1999 |
| EP | 1 147 774 A1 | 10/2001 | | WO | WO 99/61888 A2 | 12/1999 |
| EP | 0 534 033 B1 | 11/2001 | | WO | WO 00/06193 | 2/2000 |
| EP | 0 925 494 B1 | 12/2001 | | WO | WO 00/12204 | 3/2000 |
| EP | 0 748 316 B1 | 5/2002 | | WO | WO 00/36396 | 6/2000 |
| EP | 0 662 124 B1 | 6/2002 | | WO | WO 01/95815 A1 | 6/2000 |
| EP | 1 245 944 A3 | 10/2002 | | WO | WO 00/49387 | 8/2000 |
| EP | 1 249 502 A2 | 10/2002 | | WO | WO 00/54026 | 9/2000 |
| EP | 1250897 A1 | 10/2002 | | WO | WO 00/56444 | 9/2000 |
| EP | 1 380 304 A2 | 1/2004 | | WO | WO 00/70080 | 11/2000 |
| EP | 1403633 A3 | 4/2004 | | WO | WO 01/02836 A1 | 1/2001 |
| EP | 1 100 400 B1 | 5/2004 | | WO | WO 01/28700 A1 | 4/2001 |
| EP | 1 257 168 B1 | 2/2005 | | WO | WO 0129538 | 4/2001 |
| FR | 2574656 A1 | 6/1986 | | WO | WO 01/37655 A1 | 5/2001 |
| FR | A-2 635453 | 2/1990 | | WO | WO 01/40765 A2 | 6/2001 |
| FR | 2 647 668 A | 12/1990 | | WO | WO 01/42757 A2 | 6/2001 |
| FR | 2699678 A1 | 6/1994 | | WO | WO 01/51612 A1 | 7/2001 |
| GB | 2 121 976 A | 1/1984 | | WO | WO 01/61313 A2 | 8/2001 |
| GB | 2 122 369 A | 1/1984 | | WO | WO 01/68110 | 9/2001 |
| GB | 2 125 181 A | 2/1984 | | WO | WO 01/68226 A2 | 9/2001 |
| GB | 2 136 561 A | 9/1984 | | WO | WO 01/71348 A1 | 9/2001 |
| GB | 2 137 352 A | 10/1984 | | WO | WO 01/75161 A2 | 10/2001 |
| GB | 2145112 | 2/1985 | | WO | WO 0175176 | 10/2001 |
| GB | 2 144 542 A | 3/1985 | | WO | WO 01/85913 A2 | 11/2001 |
| GB | 2 153 521 A | 8/1985 | | WO | WO 01/85913 A3 | 11/2001 |
| GB | 2 243 681 A | 11/1991 | | WO | WO 01/90295 A1 | 11/2001 |
| GB | 2 360 360 A | 9/2001 | | WO | WO 02/01189 A1 | 1/2002 |
| GB | 1471019 | 2/2007 | | WO | WO 02/04666 A2 | 1/2002 |
| JP | 61139747 | 6/1986 | | WO | WO 02/19594 | 3/2002 |
| JP | 61159135 A | 7/1986 | | WO | WO 02/19943 A1 | 3/2002 |
| JP | 2024535 | 1/1990 | | WO | WO 02/20850 A2 | 3/2002 |
| JP | 4126064 A | 4/1992 | | WO | WO 02/21102 A2 | 3/2002 |
| JP | 4126065 A | 4/1992 | | WO | WO 02/23163 A1 | 3/2002 |
| JP | 4126066 A | 4/1992 | | WO | WO 02/25269 A2 | 3/2002 |
| JP | 4126079 A | 4/1992 | | WO | WO 02/26114 A2 | 4/2002 |
| JP | 4126080 A | 4/1992 | | WO | WO 02/28311 A2 | 4/2002 |
| JP | 4126081 A | 4/1992 | | WO | WO 02/29106 A2 | 4/2002 |
| SU | 1056008 | 11/1983 | | WO | 0241906 A2 | 5/2002 |
| SU | 1260778 A1 | 9/1986 | | WO | WO 02/41906 A2 | 5/2002 |
| WO | WO 84/01265 A1 | 4/1984 | | WO | WO 02/43486 A1 | 6/2002 |
| WO | WO 85/04014 A1 | 9/1985 | | WO | WO 02/43574 A2 | 6/2002 |
| WO | WO 88/07198 | 9/1988 | | WO | WO 02/44319 A2 | 6/2002 |
| WO | WO 89/04470 A1 | 5/1989 | | WO | WO 02/052244 A2 | 7/2002 |
| WO | WO 89/04471 A1 | 5/1989 | | WO | WO 02/054044 A2 | 7/2002 |

| | | |
|---|---|---|
| WO | WO 02/057775 A1 | 7/2002 |
| WO | WO 02/060880 A1 | 8/2002 |
| WO | WO 02/077637 A1 | 10/2002 |
| WO | WO 02/092161 A1 | 11/2002 |
| WO | WO 02/092247 A1 | 11/2002 |
| WO | WO 03/008102 A1 | 1/2003 |
| WO | WO 03/008937 A2 | 1/2003 |
| WO | WO 03/012403 A1 | 2/2003 |
| WO | WO 03/016875 A2 | 2/2003 |
| WO | 03020877 A2 | 3/2003 |
| WO | WO 03/056330 A2 | 7/2003 |
| WO | WO 03/056335 A2 | 7/2003 |
| WO | WO 03/ 072765 A1 | 9/2003 |
| WO | WO 03/078065 A1 | 9/2003 |
| WO | WO 03/078972 A1 | 9/2003 |
| WO | WO 04001401 | 12/2003 |
| WO | WO 2004/006916 A1 | 1/2004 |
| WO | WO 2004/009237 A2 | 1/2004 |
| WO | WO 2004/009237 A3 | 1/2004 |
| WO | WO 2004/012837 A2 | 2/2004 |
| WO | WO 2004/017041 A2 | 2/2004 |
| WO | WO 2004/024227 A2 | 3/2004 |
| WO | WO 2004/046712 A2 | 6/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 2004/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | 2006012597 A2 | 2/2006 |
| WO | WO 2006/015056 A2 | 2/2006 |
| WO | WO 2006060770 A2 | 8/2006 |
| WO | WO 2007016090 A2 | 2/2007 |

OTHER PUBLICATIONS

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, T. et al., Milk Production Evaluation in First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $in Asia B. Japan; www.agnet.org/library/article/eb384b.html.

Lopez, H. et al., Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology (1998) www.foodsci.uoguelph.ca/dairyedu/biosyntheses.html.

Milk Production, Released Jul. 18, 2006, by the National Agricultural Statistics Service (NASS), Agri. Stats. Board, US Dept of Agri.

De Vries, A. Economic Value of Pregnancy in Dairy Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reporduction, vol. 53, pp. 276-284.

Salisbury, G.W. et al., Substrate-Free Epididymal-Like Bovine Spermatozoa, J Repord Fertil, 1963, vol. 6, pp. 351-359.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel *Anguilla japonica*, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa , School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, September/October 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Sci. USA, vol. 80, pp. 1327-1331, Mar. 1983.

Zilli, L., et al. Adenosine Triphosphate Concentration and β-D-Glucuron idase Activity as Indicators of Sea Bass Semen Quality; Biology of Reproduction 70,1679-1684 (2004) Published online before print Feb. 11, 2004.

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Seidel, G.E. Jr., et al., Methods of Ovum Recovery and Factors Affecting Fertilization of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

WO 01/40765 A3 (search report), XY,Inc., Jun. 7, 2001.

WO 04/017041 A3 Search Report, XY Inc., Feb. 26, 2004.

WO 04/012837 A3 Search Report, XY, Inc., Feb. 12, 2004.

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).

Bakker Schut, Tom C. "A New Principle of Cell Sorting by Using Selective Electroportation in a Modified Flow Cytometry," University of Twente, Mar. 10, 1990.

Behrman, S. J., et al., "Freeze Preservation of Human Sperm" American Journal of Obstetrics and Gynecology vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., et al., 1999 Sexual Dimorphism in IVM-IVF Bovine Embryos Produced from X and Y Chromosome-Bearing Spermatozoa Sorted by High Speed Flow Cytometry. Theriogenology. 52: 35-48.

BigosBigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef—Production III. Culling Strategies and Nontraditional Management-Systems", J. Anim. Sci. 65:963. 1987.

Braun, J. et al, "Effect of Different Protein Supplements on Motility and Plasma Membrane Integrity of Frozen-Thawed Stallion Spermatozoa", Cryobiology (1995) 32:487-492.

Buchanan, B.R. "Pregnancy Rates in Mares Following a Single Insemination with a Low Number of Spermatozoa into the Tip of the Uterine Horn" Theriogenology p. 395.

Burns, P. D. and Spitzer, J.C., "Influence of Biostimulation on Reproduction in Postpartum Beef-Cows", J. Anim. Sci. 70:358. 1992.

Byerley, D. J., et al., "Pregnancy Rates of Beef Heifers Bred Either on Puberal or Third Estrus". J Anim. Sci. 65:645. 1987.

Cave-Penney, Tony, "Sexed Semen Offers Faster Genetic Gain", Farming News, Livestock Supplement, Feb. 1997, p. 28.

*Celestron: Telescope Basics*: www.celestron.com/tb-2ref/htm; 4 pages.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Choi, Y.H. "Developmental Cappacity of Equine Oocytes Matured and Cultured in Equine Trophoblast-Conditioned Media" Theriogenoogy 56: 320-339, 2001.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. Of Aberdeen, Scotland. 1973.

da Silva, Coutinho M.A.."Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.

*DakoCytomation, "MoFlo® Sorters"* http://www.dakocytomation.us/prod_productrelatedinformation?url=gprod_moflo_index.htm one page, printed Jun. 26, 2003.

Database up 1 BR9704313 (Alves, De Resende et al) Jun. 4, 1999.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

*Diagnostic Products Corporation, "Coat-A-Count"* http://www.Progesterone.com. 1998.

Dikeman, M. E. "Cattle Production Systems to Meet Future Consumer Demands" J. Anim. Sci. 59:1631, 1984.

Dippert, K.D. "Fertilization Rates in Superovulated and Spontaneously Ovulating Mares" Theriogenology 41: 1411-1423, 1994.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNAcontent ofLiving Spermatozoa Using Flow Cytometry Technique Journal of Reproduction and Fertility, 1993, vol. 98, pp. 357-365.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Conf. on Artificial Insemination and Reproduction, 62-70 (1984).

Fuller, Robert R. "Characterizing Submicron Vesicles With Wavelenth-Resolved Fluorescence in Flow Cytometry," University of Illinois, May 13, 1996.

Ginther, O. J., "Sexual Behavior Following Introduction of a Stallion into a Group of Mares" Therio. vol. 19 (6) Jun. 1983.

Gombe, S. and Hansel, W. "Plasma Luteinizing Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper-Mayer".

Gottlinger et al., "Operation of a Flow Cytometer", Flow Cytometry and Cell Sorting, A. Radbruch (Ed.), 1992, pp. 7-23.

Graham, J. Analysis of Stallion semen and its Relation to Fertility. Abstract Complete article from Reproductive Technology vol. 12 # 1 Apr. 1996 now included in XYIDS000213.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal Weaned Calves". I. Prod. Agric. 4:168 (1991).

Hall, J. B., et al., "Effect of Age and Pattern of Gain on Induction of Puberty with a Progestin in Beef Heifers." J. Anim. Sci. 75:1606 (1997).

Hamamatsu, "*Technical Information, Optical Detector Selection: A Delicate Balancing Act*", web page, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harte, F. J. "System of Production of Beef From Once Calved Heifers." In: J.C. Taylor (Ed.) *The Early Calving of Heifers and its Impact on Beef Production*. 123 (1975).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hohenboken, W. D. "Applications of sexed semen in cattle production." Therio. 52:1421. 1999.

Horan, Paul K. "Quantitative Single Cell Ana,lysis and Sorting, Rapid Analysis and sorting of cells is emerging as an important new technology in research and medicine."

IMV Technologies, Protocol of Bioxcell with Fresh Semen, 1 page, 2000.

IMV Technologies, Protocol of Bioxcell with Frozen Semen, 2 pages, 2000.

Iwazumi, Y., et al., "Superovulation Using CIDR in Holstein Cows" J. of Reprod. Dev. vol. 40 (3) 1994, pp. 259-266.

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production*. 10. (1975).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Successful Gender Preselection in Farm Animals", Agricultural Biotechnology, p. 439-452. (1998).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. of Agric. Research 10:281. (1971).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle—Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Laster, D. B., "Factors Affecting Dystocia and Effects of Dystocia on Subsequent Reproduction in Beef-Cattle." J. Anim. Sci. 36:695. (1973).

Lightwave Electronics, "Xcyte," www.LightwaveElecronics.com.

Liu, Z, et al. "Survival of Bull Sperm Frozen at Different rates in Media Varying in Osmolarity." Cryobiology, vol. 27, 1998, pp. 219-230.

Lu, K. H. et al., "In Vitro Fertilization of Bovine Oocytes with Flow-Cytometrically Sorted and Unsorted Sperm from Different Bulls" Therio. abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Manni, Jeff. "To-Photon Excitation Expands the Capabilities of Laser-Scanning Microscopy,"

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production.* (1975).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

Meilgaard, M., et al., "Sensor Evaluation Techniques." CRC Press Inc., Boca Raton, FL. (1991).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Moe, P. W., "Energetics of Body Tissue Mobilization." J. of Dairy Sci. 54:548.

Moran, C., et al., "Puberty in Heifers—a Review." Animal Reproduction Sci. 18:167. (1989).

Morgan, J. B., et al., "National Beef Tenderness Survey." J. Anim. Sci. 69: 3274. (1991).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001(Su;;l. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female—A Means of Increasing Meat Production." Proc. Symp. on the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Patterson, D. J., et al., "Estrus Synchronization with an Oral Progestogen Prior to Superovulation of Postpartum Beef Cows" Therio. 48, 1025-33 (1997).

Penfold, L.M.et at., "Comparative Motility of X and Y Chromosome-Bearing Bovine Sperm Separated on the Basis of DNA Content", Mol. Reprod. and Develop. 1998, vol. 50,pp. 323-327.

Petit, M. "Early Calving in Suckling Herds." In: J.C. Taylor (ed.) *The Early Calving of Heifers and its Impact on Beef Production.* p. 157-176. (1975).

Picket B.W., et al., "Livestock Production Science," 1998.

Pinkel et al., "Flow Chambers and Sample Handling", Flow Cytometry: Instrumentation and Data Analysis, Van Dilla et al. (Eds.), 1985, pp. 77-128.

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, Naouka Publishing House, 1983, pp. 181-195.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rathi, R. et al., "Evaluation of In Vitro Capacitation of Stallion Spermatoza", Biology of Reproduction 2001,vol. 65, pp. 462-470.

Recktenwald, Diether. "Cell Separation Methods and Applications," New York 1997.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (199).

Riggs, B.A. "Integration of Early Weaning and Use of Sexed Semen in a Single-Calf Heifer System to Increase Value of Non-Replacement Heifers" MS Thesis, Colorado State University, Spring 2000.

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embroynic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production.* 23. (1975).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Roy, J. H., "Rearing Dairy-Herd Replacements." Journal of the Society of Dairy Technology 31:7379 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34.

Seidel, G. E. Jr. Sexing mammalian spermatozoa and embryos—state of the art Journal of Reproduction and Fertility Supp 54, 477-487 1999.

Seidel, G. E. Jr et al., "Current Status of Sexing Mammalian Spermatozoa," Society for Reproduction and fertiity, pp. 733-743, 2002.

Seidel, G. E. Jr., "Commercilizing Reprenductive Biotechnology—The Approach used by XY, Inc.," Theriogenology, p. 5, 1999.

Seidel, G. E. Jr., et al, "Sexing Mammalian Sperm—Overview", Therio. 52: 1267-1272, (1999).

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. Md., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine.

Solsberry G.U., Van-Denmark N.L., Theory and practice of artificial cow insemination in USA, Moscow, KOLOS Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMD 532, www.specra-physics.com.

Spectra-Physics, The Solid State Laser Company, Vanguard 350-HMD 355, www.specra-physics.com.

Squires, E.L., "Procedures for Handling Frozen Equine Semen for Maximum Reproductive Efficiency", pp. 1, 39-41, 81-89.

Staigmiller, R.B. "Superovulation of Cattle with Equine Pituitary Extract and Porcine FSH" Theriogenology 37: 1091-1099 1992.

Stap J. Et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Tatum, J. D., et al., "Carcass Characteristics, Time on Feed and Cooked Beef Palatability Attributes." J. Anim. Sci. 50:833. (1980).

Thun, Rico, et al., Comparison of Biociphos-Plus® and TRIS-Egg Yolk Extender for Cryopreservation of Bull Semen; Theriogenology Symposium, Dec. 1999, vol. 52, #8.

*Time-Bandwidth Products "GE-100-XHP"*, www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

Vincent, B.C., et al, "Carcass Characteristics and Meat Quality of Once-Calved Heifers." Canadian J. Anim. Sci. 71:311. (1991).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservvation of Spermatozoa and the Assessment of Their Post-Thawing Function," Reprod. Fertil. Dev. 7:871-891 (1995) Abstract.

Wheeler, T. L., et al., "Effect of Marbling Degree on Beef Palatability in *Bos-taurus* and *Bos-indicus* cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, D. E. et al., "Mammal Species of the World", Smithsonian Institution Press, 1993, 1206 pp.

Wintzer Et al.:"Krankheiten des Pferdes Ein Leitfaden fur Studium and Praxiz," 1982, nParey, Berlin Hamburg XP002281450.

Zhou, Hongwei, et al. "Research on and Development of Flow Cell Sorting Apparatuses," Gazette of Biophysics, vol. 13, ed. 3, 1997.

Hamamatsu, "*Photomultiplier Tubes*," web page, http://www.optics.org/hamamatsu/pmt.html. Printed on Apr. 15, 2000 4.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23.

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. and Develop. 2003. vol. 15, pp. 351-359.

Hollinshead F. K. et al. "Production of lambs of predetermined sex after the insemination of ewes with low numbers of frozen-thawed sorted X- or Y-Chromosome-bearing spermatozoa", Reprod. Fertil. and Develop. 2002, vol. 14, pp. 503-508.

Hollinshead F. K. et al. "Sex-Sorting and Re-cryopreservation of Frozen-Thawed Ram Sperm for In Vitro Embryo Production" Theriogenology , vol. 59. (2003) pp. 209.

Dhali et al. Vitrification of Buffalo (*Bubalus bubalis*)Oocytes, Embryo Theriogenology vol. 53, pp. 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertiliation and AI, Journal of Animal Science,vol. 77, Suppl 2/J, Dairy Sci. vol. 82, Suppl. Feb. 1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resdolution DNA analysis of X- and Y-chromosome bearing sperm, Cytometry 25:191-199 (1996).

van Munster, E. B. Interferometry in flor to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/lsrll.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 Vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen receptors (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, (2006) pp. 15.

Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art; Animal Reproduction Science; 60-61 (2000) pp. 93-107.

"Applying Semen Sexing Technology to the AI Industry", National Association of Animal Breeders, Sep. 2000, pp. 1-16.

Akhtar, S., et al. 1995. Prevalence of Five Stereotypes of Bluetongue Virus in a Rambouillet Sheep Flock in Pakistan, Veterinary Record 136, p. 495.

Amann, R.P. and Seidel, G.E. Jr., 1982. Prospects for Sexing Mammalian Sperm, Animal Reproduction Laboratory College of Veterinary Medicine and Biomedical Sciences, Colorado State University ( ).

Amoah, E.A. and Gelaye, S. 1996. Biotechnological advances in goat reproduction. J. Anim. Sci. 75(2):578-585.

Anderson, V.K., et al., 1973. Intrauterine and tiefzervikale Insemination mit Gefriersperma bein Schat. Zuchthygiene. 8:113-118.

Baker, R.D., et al., H.W. 1968. Effect of Volume of semen, Number of sperm and drugs on transport of sperm in artificially inseminated gilts. J. Anim. Sci. 27:88-93.

Batellier, F, Vidament M, Duchamp G, Arnaud G, Yvon JM, Fauquant J, Magistrini M., Advances in cooled technologies. Anim Reprod Sci 2001; In press.

Barnes, F.L.. and Eyestone, W.H., "Early Cleavage and the Maternal Zygotic Transition in Bovine Embryos", Theriogenology, vol. 33, No. 1, Jan. 1990, pp. 141-149.

Becker, S.E. and Johnson, A.L. 1992. Effects of gonadotropin releasing hormone infused in a pulsatite or continuous fashion on serum gonadotropin concentrations and ovulation in the mare. J. Anim. Sci. 70:1208-1215.

Bedford, S .J. and Hinrichs, K. 1994. The effect of insemination volume on pregnancy rates of pony mares. Theriogenology 42:571-578.

Berger, G.S. 1987. Intratubal insemination. Fert. Steril. 48:328-330.

Beyhan, Z., et al., 1998. Sexual dimorphism in IVF bovine embryos produced by sperm sorted by high speed flow cytometry. Theriogenology. 49(1):359. abstr.

Beyhan, Z., et al., 1999. Sexual dimorphism in IVM-IVF bovine embryos produced from X and Y Chromosome-Bearing spermatozoa sorted by high speed flow cytometry. Theriogenology. 52:35-48.

Blanchard, T. and Dickson, V., "Stallion Management", The Veterinary Clinics of North America, Equine Practice, vol. 8, No. 1, pp. 207-218 (1992).

Bracher, V. and Allen, W.R., "Videoendoscopic Examination of the Mare's Uterus: Findings in Normal Fertile Mares", Equine Veterinary Journal, vol. 24 (1992), pp. 274-278.

Braselton, W.E. and McShan, W.H. 1970. Purification and properties of follicle stimulating and luteinizing hormones from horse pituitary glands. Arch. Biochem. Biophys. 139:45-48.

Brethour, J.R. and Jaeger, J.R., "The Single Calf Heifer System", Kansas Agric. Sta. Rep of Progress 570, 1989.

Bristol, S.P. 1982. Breeding behavior of a stallion at pasture with 20 mares in synchronized oestrus. J. Reprod. Fert. Suppl. 32:71.

Brookes, A. J. and Obyme, M., "Use of cow-heifers in beef production", J. of the Royal Agricultural Society of England 126:30. (1965).
Buchanan, B.R., et al, "Insemination of Mares with Low Nos. Of Either Unsexed or Sexed Spermatozoa", Theriogenology, vol. 53, pp. 1333-1344, (2000).
Burwash, L.D., et al., 1974. Relatioship of duration of estrus to pregnancy rate in normally cycling, non-lactating mares. J.A.V.M.A. 165:714-716.
Caslick, E.A., "The Vulva and the Vulvo-vaginal Orifice and its Relation to Genital Health of the Thoroughbred Mare", Cornell Veterinarian, vol. 27, 1937, pp. 178-187.
Catt, et al., "Assesment of Ram and Boar Spermatozoa During Cell-Sorting by Flow Cytometry", Reproduction Dom Animal, vol. 32, pp. 251-258 (1997).
Catt, et al., "Birth of a Male Lamb Derived from an In Vitro Matured Oocyte Fertilized by Intracytoplasmic Injection of a Single Presumptive Male Sperm", Veterinary Record 139, 1996, pp. 494-495.
Chandler, J.E., "Videomicroscopic Comparison of Bull Sperm and Leukocyte Chromosome Areas as Related to Gender", J Dairy Sci 73, pp. 2129-2135, (1990).
Chandler, J.E., et al, "Bovine Spermatozoal Head Size Variation and Evaluation of a Seperation Technique Based on this Size", Theriogeneology 52, p. 1021-1034 (1999).
Chin, W.W. and Boime, I. 1990. In: Glycoprotein Hormones. Serona Symp. Norwell, MA. pp. 19-20.
Chung, Y.G., et al., 1998. Artificial insemination of superovulated heifers with 600,000 sexed sperm. J Anim. Sci. Suppl. 1. 836:215. abstr.
Clement, F., et al., 1998. Which insemination fertilizes when several successive inseminations are performed before ovulation. 7th Int. Symp. Eq. Repro. 151. abstr.
Cran, D.G., et al. 1997. Production of Lambs by Low Dose Intrauterine Insemination With Flow Cytometrically Sorted and Unsorted Semen, Scottish Agricultural College, UK, Theriogenology, p. 267.
Cran, D.G., et al., 1993. Production of Bovine Calves Following Separation of X-Chromosome and Y-Chromosome Bearing Sperm and In Vitro Fertilisation. Vet. Rec. 132:40-41.
Cran, D.G., et al., 1995. Sex preselection in cattle: a field trial. Vet. Rec. 136:495-496.
Cui, K., "Size Differences between human X and Y Spermatozoa and prefertilization diagnosis", Molecular Human Reproduction, vol. 3, No. 1, pp. 61-67, (1997).
Cui, K., "X Larger than Y", Nature 366, p. 177-118, (1993).
Curran, S. 1998. In: Equine Diagnostic Ultrasonography. Fetal gender determination. Rantanen & McKinnon. 1st Ed. Williams and Wilkins. pp. 165-169.
Day, B.N., et al., 1998. Birth of piglets preselected for gender following in vitro fertilization of in vitro matured pig oocytes by X and Y bearing spermatozoa sorted by high speed flow cytometry. Theriogenology. 49(1):360. abstr.
Dean, P.N., et al., 1978. Hydrodynamic orientation of spermatozoa heads for flow cytometry. Biophys. J. 23:7-13.
Demick, D.S., et al.;1976. Effect of cooling, storage, glycerization and spermatozoal Nos. On equine fertility. J. Anim. Sci. 43:633-637.
DenDaas, J.H.G., et al., 1998. The relationship between the number of spermatozoa inseminated and the reproductive efficiency of dairy bulls. J Dairy Sci. 81: 1714-1723.
Dinnyes, A., et al., "Timing of the First Cleavage Post-insemination Affects Cryosurvival of In Vitro-produced Bovine Blastocysts", Molec Reprod develop 53, 1999, pp. 318-324.
Donaldson, L. E., "Effect of Insemination Regimen on Embryo Production in Superovulated Cows", The Veterinary Record, Jul. 13, 1985, pp. 35-37.
Donoghue, A.M., et al., 1996. Timing of ovulation after gonadotropin induction and its importance to successful intrauterine insemination in the tiger (*Panthera tigris*). J. Reprod. Fert. 107:53-58.
Douglas, R.H. 1979. Review of superovulation and embryo transfer in the equine. Theriogenology. 11:33-46.
Douglas, R.H., et al., 1974. Induction of ovulation and multiple ovulation on seasonally-anovulatory mares with equine pituitary fractions. Theriogenology. 2(6): 133-142.

Duchamp, G., et al., 1987. Alternative solutions to hCG induction of ovulation in the mare. J. Reprod. Fert. Suppl. 35:221-228.
Evans, M.J. and Irvine, C.H.G. 1977. Induction of follicular development, maturation and ovulation by gonadotropin releasing hormone administration to acyclic mares. Bio. Reprod. 16:452-462.
Fitzgerald, B.P., et al., 1993. Effect of constant administration of a gonadotropin-releasing hormone agonist on reproductive activity in mares: Preliminary evidence on suppression of ovulation during the breeding season. Am. J. Vet. Res. 54:1746-1751.
Fluharty, F.L., et al., "Effects of Age at Weaning and Diet on Growth of Calves", Ohio Agri. Res. and Dev. Circular, 1996, 156: 29.
Foulkes, J.A., et al., 1977. Artificial insemination of cattle using varying numbers of spermatozoa. Vet. Rec. 101:205.
Francon, M. and Yamamoto, T., "Un Noveau et tars simple dispositif interferentiel applicable as microscpe", Optica Acta 9, p. 395-408 (1962).
Fugger, E.F., "Clinical Experience with Flow Cytometric Separation of Human X- and Y-Chromosome Bearing Sperm", Theriogenology, vol. 52, pp. 1435-1440 (1999).
Fulwyler, M.J. 1965. Electronic separation of biological cells by volume. Science. 150:910.
Fulwyler, M.J. 1977. Hydrodynamic orientation of cells. J Histochem. Cytochem. 25:781-783.
Garner, D.L., et al., 1983. Quantification of the X and Y chromosome-bearing spermatozoa of domestic animals by flow cytometry. Biol. Reprod. 28:312-321.
Ginther, O.J. 1971. Some factors which alter estrus cycle in mares. J. Anim. Sci. 33:1158. abstr.
Ginther, O.J. 1992. In: Reproductive Biology of the Mare. (2nd Ed.) Equiservices, Cross Plains, WI.
Gledhill, B.L. 1988. Gender preselection: historical, technical and ethical perspective. Semin Reprod. Endocrinol. 6:385-395.
Gourley, D.D. and Riese, R.L. 1990. Laparoscopic artificial insemination in sheep. Vet. Clin. N. Amer: Food Anim. Prac. 6(3):615-633.
Grondahl, C., et al, "In Vitro Production of Equine Embryos", Biology of Reproduction, Monograph Series I, pp. 299-307 (1995).
Guillou, F. and Combamous, Y. 1983. Purification of equine gonadotropins and comparative study of their acid-dissociation and receptor-binding specificity. Biochem. Biophys. Acta. 755:229-236.
Gurnsey, M.P., and Johnson, L.A., "Recent improvements in efficiency of flow cytometric sorting of X and Y-chromosome bering sperm of domestic animals: a review", 1998, New Zealand Society of Animal Protection, three pages.
Harrison, L.A., et al., 1991. Comparison of hCG, buserelin and luprostiol for induction of ovulation in cycling mares. Eq. Vet. Sci. 3:163-166.
Hofferer, S., et al., 1993. Induction of ovulation and superovulation in mares using equine LH and FSH separated by hydrophobic interaction chromatography. J. Reprod. Fert. 98:597-602.
Holtan, D.W., et al., 1977. Estrus, ovulation and conception following synchronization with progesterone, prostaglandin F2 and human chorionic gonadotropin in pony mares. J. Anim. Sci. 44:431-437.
Householder, D.D., et al., 1981. Effect of extender, number of spermatozoa and hCG on equine fertility. J. Equine Vet. Sci. 1:9-13.
Howard, J.G., et al., 1991. Comparative semen cryopreservation in ferrets (*Mustela putorious furo*) and pregnancies after laparoscopic intrauterine insemination with frozen-thawed spermatozoa. J. Reprod. Fert. 92:109-118.
Howard, J.G., et al., 1997. Sensitivity to exogenous gonadotropins for ovulation and laparoscopic artificial insemination in the cheetah and clouded leopard. Biol. Reprod. 56:1059-1068.
Hunter, R.H.F. 1980. Transport and storage of spermatozoa in the female reproductive tract. Proc 4th Int. Congr. Anim. Repro. and A.I. 9:227-233.
Hyland, J.H., et al., 1988. Gonadotropin-releasing hormone (GnRH) delivered by continuous infusion induces fertile estrus in mares during seasonal acyclicity. Proc. Amer. Assoc. Eq. Prac. 181-190.
Irvine, C.H.G. and Alexander, S.L. 1993. In: Equine Reproduction. Edited by McKinnon and Voss. Lea and Febiger. Philadelphia, London. pp. 37.
Jafar, et al., "Sex Selection in Mammals: A Review", Theriogenology, vol. 46, pp. 191-200 (1996).

Jasko, D.J., et al., "Effect of volume and concentration of spermatozoa on embryo recovery in mares", Theriogenology. 37:1233-1239, 1992.

Jasko DJ, Moran DM, Farlin ME, Squires EL, Amann RP, Pickett BW. Pregnancy rates utilizing fresh, cooled, and frozen-thawed stallion semen. Proc 38$^{th}$ Ann Convention AAEP 1992; 649-660.

Johnson, A.L. "Pulsatile release of gonadotropin releasing hormone advances ovulation in cycling mares", Biol. Reprod. 35:1123-1130, 1986.

Johnson, A.L., et al. "Use of gonadotropin-releasing hormone (GnRH) treatment to induce multiple ovulations in the anestrous mare" Eq. Vet. Sci. 8:130-134, 1988.

Johnson, L., "Sex Preselection in Swine: Flow Cytometric Sorting of X- and Y-Chromosome Bearing Sperm to Produce Offspring", Boar Semen Preservation IV, 2000, pp. 107-114.

Johnson, L..A., "Sex Preselection in Rabbits: Live Births from X and Y Sperm Separated by DNA and Cell Sorting" Biology of Reproduction, vol. 41, pp. 199-203 (1989).

Johnson, L..A., "Advances in Gender Preselection in Swine" Journal of Reproduction and Fertility Supplement, vol. 52, pp. 255-266 (1997).

Johnson, L..A., "Sex Preselection in Swine: Altered Sex Ratios in Offspring Following Surgical Insemination of Flow Sorted X- and Y-Bearing Sperm", Reproduction in Domestic Animals, vol. 26, pp. 309-314 (1991).

Johnson, L.A. 1994. Isolation of X- and Y-bearing spermatozoa for sex preselection. In: Oxford Reviews of Reproductive Biology. Ed. HH Charlton. Oxford University Press. 303-326.

Johnson, L.A. 1995. Sex preselection by flow cytometric separation of X and Y chromosome bearing spermatozoa based on DNA difference: a review. Reprod. Fert. Dev. 7:893-903.

Johnson, L.A. 1997. Advances in gender preselection in swine. J Reprod. Fert. Suppl. 52:255-266.

Johnson, L.A., "Gender preselection in Mammals: An overview", Deutsch. Tierarztl. Wschr, vol. 103, pp. 288-291 (1996).

Johnson, L.A., "Flow cytometric determination of spermatozoa sex ratio in semen purportedly enriched for X or Y bearing spermatozoa" Theriogenology. 29:265. abstr.

Johnson, L.A., "Gender preselection in domestic animals using flow cytometrically sorted sperm" J Anim. Sci. Suppl 1.70:8-18. 1992.

Johnson, L.A., "The safety of sperm selection by flow cytometry" Ham. Reprod. 9(5):758, 1994.

Johnson, L.A., et al. "Sex Preselection: High-speed flow cytometric sorting of X and Y sperm for maximum efficiency", Theriogenology, vol. 52, (1999), pp. 1323-1341.

Johnson, L.A., et al., "Enhanced flow cytometric sorting of mammalian X and Y sperm: high speed sorting and orienting nozzle for artificial insemination", Theriogenology. 49(1):361. abstr., 1988.

Johnson, L.A., et al., "Flow sorting of X and Y chromosome bearing spermatozoa into two populations", Gam. Res. 16:203-212, 1987.

Johnson, L.A., et al., "Improved flow sorting resolution of X- and Y-chromosome bering viable sperm separation using dual staining and dead cell gating" Cytometry 17 (suppl 7) 83, 1994.

Johnson, L.A., et al."Modification of a Laser-Based flow Cytometer for High-Resolution DNA Analysis of Mammalian Spermatozoa", Cytometry 7, pp. 268-273 (1986).

Johnson, L.A.., "Flow sorting of X and Y chromosome-bearing sperm for DNA using an improved preparation method and staining with Hoechst" 33342. Gam. Res. 17:1-9, 1987.

Kachel, et al., "Uniform Lateral Orientation, Cused by Flow Forces, of Flat Particles in Flow-Through Systems", The Journal of Histochemistry and Cytochemistry, 1997, vol. 25, No. 7, pp. 774-780.

Kanayama, K., et al., 1992b. Pregnancy by means of tubal insemination and subsequent spontaneous pregnancy in rabbits. J. Int. Med. Res. 20:401-405.

Kilicarslan, M.R., et al., 1996. Effect of GmRH and hCG on ovulation and pregnancy in mares. Vet. Rec. 139:119-120.

Lapin, D.R. and Ginther, O.J. 1977. Induction of ovulation and multiple ovulations in seasonally anovulatory and ovulatory mares with an equine pituitary extract. J. Anim. Sci. 44:834-842.

Lawrenz, R. 1985. Preliminary results of non-surgical intrauterine insemination of sheep with thawed frozen semen. J S Afr. Vet. Assoc. 56(2):61-63.

Levinson, G., et al., 1995. DNA-based X-enriched sperm separation as an adjunct to preimplantation genetic testing for the preparation of X-linked disease. Mol. Human Reprod. 10:979-982.

Lindsey, A., et al., "Hysteroscopic Insemination of Mares with Nonfrozen Low-dose Unsexed or Sex-sorted Spermatozoa", currently unpublished, pp. 1-15.

Lindsey, AC, Bruemmer JE, Squires EL. Low dose insemination of mares. Animal Reproduction Science 2001; In press.

Linge, F. 1972. Faltforsok med djupfrost sperma (field trials with frozen sperm). Farskotsel. 52:12-13.

Lonergan, P., et al., "Effect of Time Interval from Insemination to First Cleavage on the Development of Bovine Embryos In Vitro and In Vivo", Theriogenology, 1999, p. 326.

Long, C.R., et al., 1998. Theriogenology. 49(1):363. abstr.

Loy, R.G. and Hughes, J.P. 1965. The effects of human chorionic gonadotropin on ovulation, length of estrus, and fertility in the mare. Cornell Vet. 56:41-50.

Macmillan, K.L. and Day, A.M., "Prostaglandin F2a : A Fertility Drug in Dairy Cattle?", Animal Research Station, Private Bag, Hamilton, New Zealand, Theriogenology, vol. 18 No. 3, pp. 245-253 (1982).

Matsuda, Y. and Tobari, I. 1988. Chromosomal analysis in mouse eggs fertilized in vitro with sperm exposed to ultraviolet light (UV) and methyl and ethyl methanesulfonate (MMS and EMS). Mutat. Res. 198:131-144.

Maxwell, W and Johnson, L. , "Chlortetracycline Analysis of Boar Spermatozoa after Incubation, Flow Cytom Sorting, Cooling, or Cryopreservation", Molecular Reproduction and Development 46, 1997, pp. 408-418.

Maxwell, W.M.C., et al., 1993. Fertility of Superovulated Ewes after Intrauterine or Oviductal Insemination with Low Numbers of Fresh or Frozen-Thawed Spermatozoa. Reprod. Fertil. Dev. 5:57-63.

Maxwell WMC, Long CR, Johnson LA,, Dorbrinsky JR, Welch GR. The relationship between membrane status and fertility of boat spermatozoa after flow cytometric sorting in the presence or absence of seminal plasma. Reprod Fertil Dev 1998; 10:433-440.

McCue, P.M. 1996. Superovulation. Vet. Clin. N. Amer. Eq. Prac. 12:1-11.

McCue, P.M., et al., 1997. Oviductal insemination in the mare. 7th Int Symp. Eq. Reprod. 133. abstr.

McDonald, L.E. 1988. Hormones of the pituitary gland. In: Veterinary Pharmacology and Therapeutics. 6th ed. Edited by N.H. Booth and L.E. McDonald. Ames, Iowa State Univ. Press. pp. 590.

McKenna, T. et al., 1990. Nonretum rates of dairy cattle following uterine body or cornual insemination. J. Dairy Sci. 73:1179-1783.

McKinnon, A.O. and Voss, J.L. 1993. In: *Equine Reproduction*. Lea and Febiger. Philadelphia, London.

McKinnon, A.O., et al., 1993. Predictable ovulation in mares treated with an implant of the GnRH analogue deslorelin. Eq. Vet. J. 25:321-323.

McKinnon, A.O., et al., 1996. Repeated use of a GnRH analogue deslorelin (Ovuplant) for hastening ovulation in the transitional mare. Eq. Vet. J. 29:153-155.

McNutt, et al., "Flow Cytometric Sorting of Sperm: Influence on Fertilization and Embryo/Fetal Development in the Rabbits", Molecular Reproduction and Development, vol. 43, pp. 261-267 (1996).

Meinert, C., et al., "Advancing the time of ovulation in the mare with a short-term inplant releasing the GnRH analogue deslorelin", Equine Veterinary Journal, 25, pp. 65-68 (1993).

Merton, J., et al., "Effect of Flow Cytometrically Sorted Frozen/Thawed Semen on Success Rate of In Vitro Bovine Embryo Production", Theriogenology 47, 1997, pp. 295.

Meyers, P.J., et al., 1997. Use of the GnRH analogue, deslorelin acetate, in a slow release implant to accelerate ovulation in oestrous mares: Vet. Rec. 140:249-252.

Michaels, Charles, "Beef A.I. Facilities that work", Proc. Fifth N.A. A.B Tech. Conf. A.I. Reprod. Columbia, MO. pp. 20-22.

Michel, T.H., et al., 1986. Efficacy of human chorionic gonadotrophin and gonadatrophin releasing hormone for hastening ovulation in Thoroughbred mares. Eq. Vet. J. 6:438-442.

Miller, S.J. 1986. *Artificial Breeding Techniques in Sheep*. In Morrow, D.A. (ed): Current Therapy in Theriogenology 2. Philadelphia, WB Saunders.

Mirskaja, L.M. and Petrapavlovskii, V.V. 1937. The reproduction of normal duration of heat in the mare by the administration of Prolan. Probl. Zivotn. Anim. Breed. Abstr. 5:387.

Molinia, F.C., et al., 1998. Successful fertilization after superovulation and laparoscopic intrauterine insemination of the brushtail possum, *Trichosurus vulpecula*, and tammar wallaby, *Macropus eugenii*. J.Reprod. Fert. 112:9-17.

Moran DM, Jasko, DJ, Squires EL, Amann RP. Determination of tempature and cooling rate which induce cold shock in stallion spermatozoa. Theriogenology 1992; 38:999-1012.

Morcom, C.B. and Dukelow, W.R. 1980. A research technique for the oviductal insemination of pigs using laparoscopy. Lab. Anim. Sci. 1030-1031.

Morris, L.H., et al., "Hysteroscopic insemination of small numbers of spermatozoa at the uterotubal junction of preovulatory mares", Journal of Reproduction and Fertility, vol. 118, pp. 95-100 (2000).

Muller, W. and Gautier, F. 1975. Interactions of heteroaromatic compounds with nucleic acids. Euro. J Biochem. 54:358.

Munne, S. 1994. Flow cytometry separation of X and Y spermatozoa could be detrimental to human embryos. Hum. Reprod. 9(5):758.

Nowshari, et al., "Superovulation of Goats with Purified pFSH Supplemented with Defined Amounts of pLH", Theriogenology, vol. 43, pp. 797-802 (1995).

Pace, M.M. and Sullivan, J.J. 1975. Effect of timing of insemination, numbers of spermatozoa and extender components on pregnancy rates in mares inseminated with frozen stallion semen. J Reprod. Fert. Suppl. 23:115-121.

Parrish, J.J. "Capacitation of Bovine Sperm by Heparin", Department of Meat and Animal Science, Biology of Reproduction 38, pp. 1171-1180 (1988).

Peippo, J., et al., "Sex diagnosis of equine preimplantation embryos using the polymerase chain reaction", Theriogenology, vol. 44 619-627 (1995).

Penfold, L.M. et al., "Comparative Motility of X and Y Chromosome-Bearing Bovine Sperm Separated on the Basis of DNA Content", Mol. Reprod. and Develop. 1998, vol. 50, pp. 323-327.

Perry, E.J. 1968. Historical Background In: *The Artificial Inseminalion of Farm Animals*. 4th ed. Edited by E.J. Perry. New Brunswick, Rutgers University Press, pp. 3-12.

Petersen, G.A., et al, "Cow and Calf Performance and Economic Considerations of Early Weaning of Fall-Born Beef Claves", J. Anim. Sci., 1987, 64:15, pp. 15-22.

Pickett, B.W, et al., 1976. Factors influencing the fertility of stallion spermatozoa in an A.I. program. Proc. 8th Internat. Congr. Anim. Reprod. A.I. Krakow, Poland. 4: 1049-1052.

Pickett, B.W. and Back, D.G. 1973. Procedures for preparation, collection, evaluation and insemination of stallion semen. C.S.U. Exp. Sta. Artira. Reprod. Lab. Gen. Series Bull. 935.

Pickett, B.W., and Shiner, K.A., "Recent developments in artificial insemination in horses", Livestock Production Science, 40, pp. 31-36 (1994).

Pickett, B.W., et al., 1974. The effect of extenders, spermatozoal numbers and rectal palpation on equine fertility. Proc. Fifth N.A.A.B Tech. Conf. A.I. Reprod. Columbia, MO. pp. 20-22.

Pickett, B.W., et al., 1975b. Effect of seminal extenders on equine fertility. J. Anim. Sci. 40:1136-1143.

Pickett, B.W., et al., 1978. Influence of seminal additives and packaging systems on fertility of bovine spermatozoa. J. Anim. Sci. Suppl. II. 47:12.

Pickett, B.W., et al., 1989. Management of the mare for maximum reproductive efficiency. C.S.U. Anim. Repro. Lab. Bull. No. 06. Fort Collins CO.

Pinkel, D., et al; "Flow Cytometric Determination of the Proportions of X- and Y-Chromosome-Bearing Sperm in Samples of Purportedly Separated Bull Sperm", Journal of Animal Science, vol. 60, pp. 1303-1307 (1998).

Pinkel, D., et al., 1982b. High resolution DNA measurements of mammalian spermatozoa. Cytometry. 3:1-9.

Province CA, Squires EL, Pickett BW, Amann RP. Cooling rates, stroage temperatures and fertility of extended equine spermatozoa. Theriogenlolgy 1985; 23:925-934.

Rath, D., et al., "Low Dose Insemination Technique in the Pig", Boar Semen Preservation IV, 2000, pp. 115-118.

Rath, D., et al., "Production of Piglets Preselected for Sex Following in Vitro Fertilization with X and Y Chromosome-Bearing Spermatozoa Sorted by Flow Cytometry", Theriogenology, 47, pp. 795-800 (1997).

Reiling, B.A., et al., "Effect of Prenatal Androgenization on Preformance, Location, and Carcass and Sensory Traits on Heifers in Single Calf Heifer System", J. Anim. Sci., 1995, 73: 986, pp. 986-992.

Rens, W., et al., "A Novel Nozzle for More Efficient Sperm Orientation to Improve Sorting Efficiency of X and Y Chromosome-Bearing Sperm", Technical Notes, Cytometry 33, 1998, pp. 476-481.

Rens, W., et al., "Improved Flow Cytometric Sorting of X- and Y-Chromosome Bearing Sperm: Substantial Increase in Yield of Sexed Semen", Molecular Reproduction and Development, 1999, pp. 50-56.

Rieger, D., et al, "The Relationship Between the Time of First Cleavage of Fertilized Cattle Oocytes and Their Development to the Blastocyst Stage", Theriogenology, 1999, pp. 190.

Rigby SL, Lindsey AC, Brinsko SP, Blanchard TL, Love CC, Varner DD. Pregnancy rates on mares following hysteroscopic or rectally-guided utero-tubal insemination with low sperm numbers. Proc $3^{rd}$ International Symposium on Stallion Reproduction 2001; 49 (abstr.).

Ritar, A. and Ball, A. 1991. Fertility of young cashmere goats after laparoscopic insemination. J. Agr. Sci. 117:271-273.

Roberts, J.R. 1971. In: Veterinary Obstetrics and Genital Diseases. Ithaca, New York. pp. 740-749.

Roser, JF., et al., 1980. Reproductive efficiency in mares with anti-hCG antibodies. Proc 9th Int. Congr. Anim. Repro. and A.I. 4:627. abstr.

Roth, T.L., et al., 1997. Effects of equine chorionic gonadotropin, human chorionic gonadotropin, and laparoscopic artificial insemination on embryo, endocrine, and luteal characteristics in the domestic cat. Bio Reprod. 57:165-171.

Rowley, H-S., et al., 1990. Effect of insemination volume on embryo recovery in mares. J. Equine Vet. Sci. 10:298-300.

Salamon, S. 1976. Artificial Insemination of Sheep. Chippendale, New South Whales. Publicity Press. p. 83-84.

Salisbury, G.W. and VanDemark, N.L. 1961. Physiology of Reproduction and Artificial Insemination of Cattle. San Francisco: Freeman and Company.

SAS, SAS/STAT® User's Guide (Release 6.03), SAS Inst. Inc., Cary, NC., 1988.

Schenk, J.L., "Cryopreservation of flow-sorted bovine spermatozoa", Theriogenology, vol. 52, 1375-1391 (1999).

Schenk, J.L. and Seidel, Jr., G.E., "Imminent Commercialization of Sexed Bovine", Proceedings, The Range Beef Cow Symposium XVL, 1999, pp. 89-96.

Schmid R.L., et al, "Fertilization with Sexed Equine Spermatozoa Using Intracytoplasmic Sperm Injection and Oviductal Insemination", 7th International Symposium on Equine Reproduction, pp. 139 (Abstract) (1998).

Seidel, G. Jr., "Use of Sexed Bovine Sperm for In Vitro Fertilization and Superovulation", Animal Reproduction and Biotechnology Laboratory, Colorado State University, Proceedings of the 2000 CETA/ACTE Convention, Charlottetown, Prince Edward Island, Aug. 2000, pp. 22-24.

Seidel, G.E. Jr, et al., "Artificial Insemination of Heifers with Cooled, Unfrozen Sexed Semen ", Theriogenology, vol. 49 pp. 365 (Abstract) (1998).

Seidel, G.E. Jr, et al., "Insemination of Heifers with Sexed Sperm ", Theriogenology, vol. 52, pp. 1407-1421 (1999).

Seidel, G.E. Jr., "Uterine Horn Insemination of Heifers With Very Low Numbers of Nonfrozen and Sexed Spermatozoa", Atlantic Breeders Cooperative, Theriogenology 48: pp. 1255-1264, (1997).

Seidel, G.E. Jr., et al., 1998. Artificial insemination of heifers with cooled, unfrozen, sexed semen. 1998. Theriogenology. 49(1):365. abstr.

Seidel, G.E. Jr.,et al., 1999. Insemination of heifers with sexed frozen or sexed liquid semen. Theriogenology. 51. (in press). abstr.

Seidel, G.E., "Status of Sexing Semen for Beef Cattle", Texas A&M University 45th Annual Beef Cattle Short Course and Trade Show Proceedings, Aug. 9-11, 1999; pp. III 24-III 27.

Seidel, Jr., G. E., "Artificial Insemination With X-and Y-Bearing Bovine Sperm", Animal Reproduction and Biotechnology Laboratory, Colorado State University, (1996).

Seidel, Jr., G. E., et al, "Insemination of Holstein Heifers With Very Low Numbers of Unfrozen Spermatozoa", Colorado State University, Atlantic Breeders Cooperative, (1995).

Seidel, Jr., G.E.et al, "Insemination of Heifers With Very Low Numbers of Frozen Spermatozoa", Colorado State University (1996).

Senger, P.L., et al., 1988. Influence of cornual insemination on conception rates in dairy cattle. J Anim. Sci. 66:3010-3016.

Shelton, J.N. and Moore, N.W. 1967. The response of the ewe tot pregnant serum mare gonadotropin and to horse anterior pituitary extract. J. Reprod. Fert. 14:175-177.

Shilova, A.V., et al., 1976. The use of human chorionic gonadothrophin for ovulation date regulation in mares. VIIIth Int. Congr. on Anim. Repro. and A.I. 204-208.

Squires, E., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, pp. 127-130 (1996).

Squires, E.L, et al., 1994. Effect of dose of GnRH analogue on ovulation in mares. Theriogenology. 41:757-769.

Squires, E.L., "Early Embryonic Loss" in Equine Diagnostic Ultrasonography, 1$^{st}$ Ed. pp. 157-163 Eds Rantanen & McKinnon. Williams and Wilkins, Baltimore, Maryland (1998).

Squires, E.L.., et al, "Cooled and frozen stallion semen", Bulletin No. 9, Colorado State University, Ft. Collins, CO. (1999).

Sullivan, J.J., et al., 1973. Duration of estrus and ovulation time in nonlactating mares given human chorionic gonadotropin during three successive estrous periods. J.A.V.M.A. 162:895-898.

Sumner, A.T. and Robinson, J.A., "A Difference in Dry mass between the heads of X and Y-bearing human Spermatozoa", J Reprod Fert 48, p. 9-15 (1976).

Taljaard, T.L., et al., 1991. The effect of the laparoscopic insemination technique on the oestrus cycle of the ewe. J. S Afr. Vet. Assoc. 62(2):60-61.

Taylor, C.S., "Efficiency of Food Utilization in Traditional and Sex-Controlled Systems of Beef Production", AFRC Animal Breeding Research Organization, West Mains Road, Edinburg EH9 3JQ, pp. 401-440.

Tervit, H.R., et al., "Successful Culture In Vitro of Sheep and Cattle Ova", Agricultural Research Council, Unit of Reproduction Physiology and Biochemistry, University of Cambridge, 1972, p. 493-497.

Van Munster E.B., et al, "Difference in volume of X- and Y-chromosome Bearing Bovine Sperm Heads Matches Difference in DNA Content" Cytometry 35 p. 125-128 (1999.

Van Munster E.B., et al, "Measurement-based evaluation of optical pathlength distributions reconstructed from simulated differential interference contrast images", Journal of Microscopy 192, Pt. 2, p. 170-176 (1998).

Van Munster, E.B., "Geslachtsbepaling met interferometrie", Derde prijs NtvN-prijsvraag voor pas-gepromoveerden 65/4, p. 95-98 (1999).

Van Munster, E.B., et al, "Difference in Sperm Head Volume as a Theoretical Basis for Sorting X & Y-Bearing Spermatozoa: Potentials and Limitations", Theriogenology 52, pp. 1281-1293, (1999).

Van Munster, E.B., et al, "Reconstruction of optical pathlength distributions form images obtained by a wide field differential interference contrast microscope", Journal of Microscopy 188, Pt. 2, p. 149-157 (1997).

Vazquez, J. et al., "Nonsurgical Uterotubal Insemination in the Mare", Proceedings of the 44th Annual Convention of the American Association of Equine Practitioners, vol. 44, pp. 68-69 (1998).

Vazquez, J., et al., "A.I. in Swine; New Strategy for Deep Insemination with Low Number of Spermatozoa Using a Non-surgical Methodology", 14$^{th}$ International Congress on Animal Reproduction, vol. 2, Stockhlom, Jul. 2000, p. 289.

Vazquez, J., et al., "Successful Low-Dose Insemination by a Fiberoptic Endoscope Technique in the Sow", Proceedings Annual Conference of the International Embryo Transfer Society, Netherlands, Theriogenology, vol. 53, Jan. 2000, pp. 201.

Vazquez, J., et al.,"Development of a Non-surgical Deep Intra Uterine Insemination Technique", Boar Semen Preservation IV, IVth International Conference on Boar Semen Preservation, Maryland, pp. 262-263.

Vazquez, J., et al.,"Hypoosmotic Swelling Test as Predictor of the Membrane Integrity in Boar Spermatozoa" , Boar Semen Preservation IV, IVth International Conference on Boar Semen Preservation, Maryland, pp. 263.

Vidament, M., et al., 1997. Equine frozen semen freezeability and fertility field results. Theriogenology. 48:907.

Vogel, T., et al, "Organization and expression of bovine TSPY", Mammalian Genome, vol. 8, pp. 491-496 (1997).

Voss, J.L. and Pickett, B.W. 1976. Reproductive management of the broodmare. C.S.U. Exp. Sta. Anim. Reprod. Lab. Gen. Series. Bull. 961.

Voss, J.L., et al., 1974. Effect of human chorionic gonadotropin on duration of estrous cycle and fertility of normally cycling, nonlactating mares. J.A.V.M.A. 165:704-706.

Voss, J.L., et al., 1982. Effect of number and frequency of inseminations on fertility in mares. J. Reprod. Fertil. Suppl. 32:53-57.

Welch G.R., et al., 1994. Fluidic and optical modifications to a FACS IV for flow sorting of X- and Y-chromosome bearing sperm based on DNA. Cytometry 17 (suppl. 7): 74.

Welch, G., et al., "Flow Cytometric Sperm Sorting and PCR to Confirm Separation of X- and Y-Chromosome Bearing Bovine Sperm", Animal Biotechnology, 6, pp. 131-139 (1995).

Wilson, C.G., et al., 1990. Effects of repeated hCG injections on reproductive efficiency in mares. Eq. Vet. Sci. 4:301-308.

Wilson, M.S. 1993. Non-surgical intrauterine artificial insemination in bitches using frozen semen. J.Reprod. Fert Suppl. 47:307-311.

Windsor, D.P., et al, "Sex Predetermination by Seperation of X and Y Chromosome-bearing Sperm: A Review", Reproduction of Fertilization and Developement 5, pp. 155-171, (1993).

Woods, J. and Ginther, O.J. 1983. Recent studies related to the collection of multiple embryos in mares. Theriogenology. 19:101-108.

Woods, J., et al., 1990. Effects of time of insemination relative to ovulation on pregnancy rate and embryonic-loss rate in mares. Eq. Vet. J. 22(6):410-415.

XP-002103478, File Biosis, (1988), one page (same as:Hawk, H.W., et al., "Fertilization Rates in Superovulating Cows After Deposition of Semen on the Infundibulum Near the Uterotubal Junction or After Insemination with High Numbers of Sperm", XP-002103478, Theriogenology, vol. 29, No. 5, pp. 1131-1142 (1988).

Parallel Chinese Application No. 03819362.0; Office Action dated Mar. 28, 2008.

Parallel Australian Application No. 2003265471; Examinati0n Report dated May 3, 2008.

Bavister, B.D. et al., The effects of Sperm Extracts and Energy Sources on the Motility and Acromosome Reaction of hamster Spermatozoa in vitero; Biology of Reproduction 16, 228-237 (1997).

Fattouh, El-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Ferre, L., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fetilization Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System. 1998 J Dairy Sci. 81: 1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times AI of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (*Anser anser* L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

Johnson L.A., et al. Use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Rath, D., "On the Status of Sex-Specific Sperm Sorting" Review lecture ET Conference 2002, Department of Animal Production and Animal Behaviour, Mariensee, Germany.

Grossfeld, R., "Experiments to Improve the Quality of Sex-Sorted Fresh and Frozen Porcine Spermatozoa" PhD thesis of the Faculty of Agricultural Sciences, Georg-August University, Gottingen, May 2007.

de Graaf, S.P. et al., Birth of offspring of pre-determined sex after artificial insemination of frozen-thawed, sex-sorted and re-frozen-thawed ram spermatozoa, Theriogenology, 67 (2007) 391-398.

O'Brien, J.K. et al., Development fo sperm sexing and associated assisted reproductive technology for sex preselection of captive bottlenose dolphins, Reproduction Fertility and Development, 2006, 18, 319-329.

Zhang, M, et al., In vitro fertilization with flow-sorted buffalo sperm, Reproduction Fertility and Development, 2005, 18(2), 283-284.

Schenk, J.L. et al., Insemination of cow elk with sexed frozen semen, 2003 Theriogenology 59, 514.

BD Biosciences Brochure, BD FACSCalibur Flow Cytometer, the Automated, Multicolor Flow Cytometry System, 2006.

Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.

Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.

Presicce, G.A., et al., First established pregnancies in mediterranean italian buffaloes (*Bubalus bubalis*) following deposition of sexed spermatozoa near the utero tubal junction, Reproduction in Domestic Animals, vol. 40, No. 1, Feb. 2005 , pp. 73-75(3).

Dielemann, S.J., Superovulation in cattle: from understanding the biological mechanisms to genomics of the oocyte; $23^{rd}$ Annual Meeting A.E.T.E.—Alghero; Sep. 2007.

Hasler, J. F., Factors influencing the success of embryo transfer in cattle; $23^{rd}$ World Buiatrics Congress, Quebec, Canada Jul. 2004.

Mapletoft, R. J. et al., Superovulation in perspective, Bioniche Animal Health, Dec. 2002.

Bahr, G.F.et al., Considerations of volume, mass, DNA, and arrangement of mitochondria in the midpiece of bull spermatozoa, Experimental Cell Research 60 (1970) 338-340.

Baumber, J., et al., "The Effect of Reactive Oxygen Species on Equine Sperm Motility, Viability, Acrosomal Integrity, Mitochondrial Membrane Potential, and Membrane Lipid Peroxidation", 2000, Journal of Andrology, vol. 21 (6),pp. 895-902.

BD L, SR II Flow Cytometer, BD Biosciences Clontech Discovery labware Immunocytometry systems Pharmingen Jan. 28, 2004.

Bermudez, D.et al., The immediate effect of IR, laser radiation on rat , germ, cells, was studied by cytophotometric quantification, Scisearch 2001.

Sequent Biotechnologies Inc., Welcome to the Sequent Biotechnologies Inc. website., http://www.sequentbiotech.com/ Dec. 6, 2003.

Sabuer K. et al."Effects of Angiotensin II on the Acrosome Reaction in Equine Spermatozoa" Journal of Reproduction and Fertility vol. 120, 2002 p. 135-142.

Brooks, D.E., Manipulation of Mammalian Gametes in Vitro, Biennial Report, Waite Agricultural Research Institute 1986-1989.

Bruemmer, J.E. et al., "Effect of Pyruvate on the Function of Stallion Spermatozoa Stored for up to 48 Hours", Journal of Animal Science 2002, vol. 80*1, pp. 12-18.

Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).

Chaudhry, P., et al., Casein Kinase II activity and polyamine-stimulated protein phosphorylation of cytosolic and plasma membrane protiens in bovine sperm, Archives of Biochemistry and Biophyeics vol. 271, No. 1 pp. 98-106, May 15, 1989.

Chen, Y. et al., Effects of sucrose, trehalose, hypotaurine, taurine, and blood serum on survival of frozen bull sperm, Cryobiology 30,423-431 (1993).

Chapter 16 Semen processing, storage, thawing, and handling, http://nongae.gsnu.ac.kr/~cspark/teaching/chap16.html Sep. 23, 2002.

Conover, J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).

Cressman, B.E. MD, et al., Effect of sperm dose on pregnancy rate from intrauterine insemination: a retrospective analysis, Texas Medicine, 92:74-79 (1996).

Crissman, H.A. et al., Use of DIO-C5-3 to improve hoechst 33342 uptake, resolution of DNA content, and survival of CHO cells, Experimental cell research 174: 338-396 (1988).

Graves, C.N., et al., "Metabolism of Pyruvate by Epididymal-Like Bovine Spermatozoa", 1964 Journal of Dairy Science vol. 47 (12), pp. 1407-1411.

Certified Semen Services, CSS Minimum requirements for disease control of semen produced for AI, http://www.naab-css.org/about_css/disease_control-2002.html Sep. 22, 2003.

Culling, "Handbook of Histopathological and Histochemical Techniques," 3rd Ed., Butterworths, pp. 192.

De Grooth, B. et al., Simple delay monitor for droplet sorters, Cytometry 12:469-472 (1991).

Lodge, J.R., et al., "Carbon Dioxide in Anaerobic Spermatozoan Metabolism" 1968, Journal of Dairy Science, vol. 51(1), pp. 96-103.

Delgado, N. et al., Correlation between sperm membrane destabilization by heparin and aniline blue staining as membrane integrity index, Archives of Andrology40:147-152 (1998).

Denniston, D.J. et al., "Effect of Antioxidants on the Motility and Viability of Cooled Stallion Spermatozoa", Journal Reproduction Supplement 56, 2001, pp. 121-126.

De Pauw M.C. et al. Sperm Binding to Epithelial Oviduct Explants in Bulls with Different Nonreturn Rates Investigated with a new In-Vitro Model Biology of Reproduction, 2002, vol. 67 p. 1073-1079.

Donoghue, A. et al., Effects of water- and lipid-soluble antioxidants on turkey sperm viability, membrane integrity, and motility during liquid storage, Poultry Science 76:1440-1445 (1997).

Durack, Gary; "Cell—Sorting Technology", Emerging Tools for Single-cell Analysis, Chapter 1 pp. 1-359.

Zucker, R. et al., Utility of light scatter in the Morphological analysis of sperm, Cytometry 13:39-47 (1992).

Ericsson, S. et al., Interrelationships among fluorometric analyses of spermatozoal function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antiobiotic Combination", Theriogenology, 1990, vol. 33(6), pp. 1211-1220.

Cho, et al. A microfluidic device for separating motile sperm from nomotile sprem via inter-streamline crossings.

Ericsson, R. et al., Functional differences between sperm bearing the X- or Y-chromosome.

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D. et al., Physiology and Management, Rapid determination on sperm cell concentration in bovine semen by flow cytometry, J Dairy Sci. 76: 86-94 (1993).

Farrell et al., "Quantification of Bull Sperm Characteristics measured by Computer-Assisted Sperm Analysis (CASA) and the Relationship of Fertility", Theriogenology, 1998, vol. 49 (4), pp. 871-879.

Fitzgerald, D., Cell sorting: An enriching Experience, The Scientist Jul. 23, 2001.

Foote, R., The history of artificial insemination: Selected notes and notables, American Society of Animal Science (2002).

Foote, R., Functional differences between sperm bearing the X- or Y-chromosome.

Garner, D., Past, Present and future perspectives on sexing sperm, CSAS Symposium SCSA: 67-78.

Zhanga, M. et al., Development of bovine embryos after in vitro fertilization of oocytes with flow cytometrically sorted, stained and unsorted sperm from different bulls, Abstract: Theriogenology vol. 60 Issue 9,pp. 1657-1663, Dec. 2003.

Johnson, L. et al., Sex preselection in mammals by DNA: A method for flow separation of X and Y Spermatozoa in humans.

Johnson, L. et al., Recent advances in sex preselection of cattle: Flow cytometric sorting of X- &Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 ( 1994).

Pinkel, D. et al., Flow cytometry of mammalian sperm progress in DNA and morphology measurement, The Journal of Histochemical and Cytochemistryvol.27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Salisbury, G.W., et al., Reversal by Metabolic Regulators of $CO_2$-induced Inhibition of Mammalian Spermatozoa, 1959, Proc Soc Exp Biology Med, vol. 101 (1) pp. 187-189.

Centola, G. et al., Cryopreservation of human semen. Comparison of cryopreservatives, sources of variability, and prediction of post-thaw survival. PMID: 1601749 May-Jun. 1992.

Bencic, D.C., et al., "Carbon Dioxide Reversibly Inhibits Sperm Motility and Fertilizing Ability in Steelhead (*Oncorhynchus mykiss*)" 2000, Fish Physiology and Biochemistry, vol. 23(4), pp. 275-281.

Boatman, D.E. et al., "Bicarbonate Carbon Dioxide Regulation of Sperm Capacitation Hyperactivated Motility and Acrosome Reactions", 1991, Biology of Reproduction vol. 44(5), pp. 806-813.

Garcia, M.A. et al., "Development of a Buffer System for Dialysis of Bovine Spermatozoa Before Freezing III.Effect of Different Inorganic and Organic Salts on Fresh and Frozen-Thawed Semen", 1989, Theriogenology, vol. 31(5),pp. 1039-1048.

Courtens, J. et al., Numerical simulation for freezing and thawing mammalian spermatozoa. Evaluation of cell injuries at different depths in bags or straws during all steps of the technique.

Eiman, M. et al., Trehalose-enhanced fluidity of the goat sperm membrane and its protection during freezing, Biology of Reproduction 69: 1245-1250 (2003).

Foote, R. et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62: 143-172 (2000).

Johnson, L. et al., Erratum to "Storage of bull semen", Animal Reproduction Science 62: 143-172 (2000).

McNutt, T. et al., Electrophoretic gel analysis of Hoechst 33342 stained and flow cytometrically sorted bovine sperm membrane proteins, Reprod. Dom Anim.31: 703-709 (1996).

Van der Werf, Julius, An overview of animal breeding programs; Animal Breeding Use of New Technologies (This is a Post Graduate Foundation Publication).

Best, T. P. et al. "Nuclear Localization of Pyrrole-Imidazole Ployamide-Flourescein Conjugates in Cell Culture", PNAS, 2003, vol. 100(21), pp. 12063-12068.

Gygi, M.P., et al. "Use of Fluorescent Sequence-Specific Polyamides to Discriminate Human Chromosomes by Microscopy and Flow Cytometry", Nuci Acids Res. 2002, vol. 30(13),pp. 2790-2799.

Young, L. et al., Prolonged feeding of low levels of zearalenone to young boars.

BD Biosciences, BD AccuDrop Potion, www.bdbiosciences.com, Sep. 2002.

Agarwal, A. et al., Filtration of spermatozoa through L4 membrane:a new method, Fertility and Sterility, vol. 06, No. 6, Dec. 1991.

Anzar, M. et al., Optimizing and Quantifing fusion of liposomes to mammalian sperm using resonance energy transfer and flow cytometric methods, Cytometry49:22-27 (2002).

Anzar, M. et al., Sperm Apoptosis in fresh and cryopreserved bull semen detected by flow cytometry and it's relationship with fertility, Biology of Reproduction 66: 354-360 (2002).

Arav, A. et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. and Cytochem., 1977, vol. 25(7), pp. 585-589.

Arts,E.et al.,Evidence for the existence of lipid-diffusion barriers in the equatorial segment of human spermatozoa, Boichem J.384:211-218 (1994).

Garner,D.et al., Spermatozoa and Seminal Plasma, Reproduction in farm animals 7th edition.

Gadella B,et al., Dynamics in the membrain organization of the mammalian sperm cell and functionality in fertilization, Vet Quart. 21:142-146 (1999).

Garner, D.et al., Chromatin stability in sex-sorted sperm, VII International Congress of Andrology.

Garner,D. et al., Morphological and ultrastrutural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and separating X- and Y-Chromosome-bearing mammalian sperm by flow cytometry, Lawrence Livermore National Laboratory, Feb. 8, 1984.

Gledhill, B.et al., Identifing X- and Y-chromosome-bearing sperm by DNA content:Retrospective perspectives and prospective opinions.

Gledhill, B.et al., Flow microflurometric analysis of sperm DNA contemt: Effect of cell shape on the fluorescence distribution, J. Cell Physiol.87: 367-378.

Gledhill, B.et al., Flow cytometry and sorting of sperm and male germ cells, Flow Cytometry and sorting, second edition, pp. 531-551 (1990).

Gordon et al., "Genetic Transformation of Mouse Embryos by Microinjection of Purified DNA", Proc. Natil Acad. Sci., 1980, vol. 77 (12), pp. 7380-7384.

Graham, J.et al.,Analysis of sperm cell viability, Acrosomal integrity, and Mitocondrial function using flow cytometry, Biology of Reproduction 43: 55-64 (1990).

Graham, J.et al., Effect of some Zwitter Ion buffers on freezing and storage of spermatozoa I, Bull, J. Dairy Sci 55: 372-378 ( 1992).

Grogan, W. et al., DNA Analysis and sorting of viable mouse testis cells, The Journal of Histochemistry and Cytochemistry, vol. 29 No. 6 pp. 738-746, (1981).

Guthrie, et al., "Flow Cytometric Sperm Sorting: Effects of Varying laser Power on Embryo Development in Swine", Mol. Reprod. and Develop., 2002,vol. 61 (1), pp. 87-92.

Hacker-Klom, U.B., et al., Effect of doxorubicin and 4'-epi-doxorubicin on mouse spermatogenesis. Mutation Research International Journal on Mutagenesis vol. 159, pp. 39-46. 1986.

Hargrove, T. et al., Special Techniques, Part B Cryopreservation, Chapter 11B.

Hasler, J., Symposium: Reproductive Technology and Genetic improvementJ. Dairy Sci. 75:2857-2879 (1992).

Held, A.et al., Quasi-CW Solid-state lasers Expand their reach, Photonics Spectra, Dec. 2002.

Hinkley, R.et al., Rapid visual detection of sperm-egg fusion using the DNA-Specific Fluorochrome Hoechst 33342, Developmental Biology 118: 148-154 (1986).

Januskauskas, A.et al.,Assessment of sperm quality through Fluorometry and sperm chromatin structure assay in relation to field fertility of frozen-thawed semen from Swedish AI bulls, Theriogenology 55: 947-961 (2001).

Janendran, R.et al., Effect of glycerol and cryopreservation on oocyte penetration by human spermatozoa, PMID: 4025843, Jul. 6, 2006.

Johnson, L., A flow cytometric/ sorting method for sexing mammalian sperm validated by DNA analysis and live births, Cytometry, p. 42 of supplement , Sep. 4, 1990.

Johnson, L., Flow sorting of intact X & Y chromosome-bearingmammalian spermatozoa, The Journal of the Society for Analytical Cytology Cytometry, (1988).

Zhang,M. et al., Development of bovine embryos after in vitro fertilzation of oocytes with a flow cytometrically sorted, stained and unsorted sperm from different bulls, Theriogenology 60: 1657-1663 (2003).

Jones,R.et al., Effect of Osmolality and Phosphate, "Tris", "Tes", "Mes", nd "Herpes" Hydrogen ion buffers on the motility of bull spermatozoa stored at 37 or 5° C., Ausi J. Biol. Sci.25:1047-1055 (1972).

Jones,R., Plasma membrane structures and remodelling during sperm maturation in the epididymis, Journal of Reproduction and Fertility (1998).

Gerrits, Roger J. Application of Biotechnology to Animal Production US Dept. of Agriculture, Beltsville Maryland.

Johnson, L., Separation of X and Y Chromosome-bearing mammalian sperm by DNA content cytometric analysis and sorting, US Department of Agriculture.

Johnson, M.,The Macromolecular Organization of membranes and its bearing on events leading up to Fertilization, Journal of Reproduction and Fertility (1975).

Johnson, L., Verified Sex Pre-Selection in Farm Animals.

Johnson, L., Progress towards achieving sex preselection in farm animals, USDA Agricultural Research Service, (1989).

Keeler, K.et al., Flow microfluorometric analysis of living spermatozoa stained with Hoechst 33342, J. Reprod.Fert. 68:205-212 (1983).

Keij, J.et al., High speed Photodamage cell sorting: An evaluation of the Zapper Prototype, Methods in cell Biology vol. 42, (1994).

Kirchhoff, C.et al., The Molecular biology of the sperm surface:Post-Testicular Membrane Remodelling, The Fate of the Male Germ Cell, (1997).

Krueger, C.et al.,Low dose Insemination in synchronized gilts, Theriogenology 52: 1363-1373 (1999).

Landetie,J.,Induction and survival of micronuclei in rat spermatids. Comparison of two meiotic micronucleus techniques using cyclophosphamide, Mutation Research, 203:47-53 (1988).

Laser Innovations—Applications, http://www.laserinnovations.com/488nm.htm Feb. 2, 2004.

Libbus, B.et al.,Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stain, Hoechst 33342, The Journal of Histochemistry and Cytochemistry,vol. 28, No. 1, pp. 36-39 (1980).

Lucas, J.et al., Orientation measurments of microsphere doublets and metaphase chromosomes in flow, Cytometry 7:575-581 (1986).

Luttmer, S.et al.,Examination of living and fixed gametes and early embryos stained with supravital fluorochromes (Hoechst 33342 and 3,3'-dihexyloxacarocyanine Iodide), Gamete Research 15:267-283 (1986).

Masiki, J.et al., Effect of bull seminal plasma on the membrane characteristics of boarepididymal spermatozoa.

Maxwell, W.et al.,Physiology of spermatozoa at high dilution rates:The influence of seminal plasma, Theriogenology 52: 1353-1362 (1999).

Mazur, P., The role of Intracellular freezing in the death of cells cooled at supraoptimal rates, Cryobiology 14:251-272 (1977).

McSweeney,K.et al., Abstract: Insemination of lactating holstein cows with sexed frozen/thawed sperm, http://www.cvmbs.colostate.edu/physio/abstract/ges12.html Mar. 16, 2004.

Medeiros,C. et al., Current status of sperm cryopreservation: Why isn't it better? Theriogenology 57: 327-344 (2002).

Meistrich, M., Potential and limitations of physical methods for separation of sperm bearing an X- or Y-chromosome.

Meistrich, M.et al., "Cytogenetic" studies of spermatids of mice carrying Cattanach's translocation by flow cytometry, Chromosoma 74:141-151 (1979).

Morrell, J. et al., Offspring from inseminations with mammalian sperm stained with Hoechst 33342, either with or without flow cytometry, Mutation Research 224:177-183 (1989).

Morrell et al.,"Sexing of Sperm by Flow Cytometry", The Veterinary Record, 1988, pp. 322-324.

Morrier, A.et al., Glycerol addition and conservation of fresh and crypreserved ram spermatozoa, Canadian Journal of AnimalScience, Sep. 2002http://pubs.nrc-cnrc.gc.ca/aic-journals/2002ab/cjas02/sep02/cjas01-045.html.

Moruzzi, J., Selecting a mammalian species for the separationof X- and Y chromosome-bearing spermatozoa, J. Reprod. Fert. 57:319-323 (1979).

Murthi S. et al., Improved data acquisition system for digital flow cytometry, (2002).

Studt, T., MEMS-based Cell Sorter Speeds Clinical Studies, R& D Magazine, Dec. 2003: pp. 36-37 as currently presented on and printed from http;//www.rdmag.com 2 pgs.

Gwo-Bin, L.et al., Multi-cell-line micro flow cytometers with buried SU-8/SOG Optical waveguides, Feb. 2002.

Shapiro, H. M. et al., Multistation Multparameter Flow Cytometry: Some Influences of Instrumental Factors on System Performance, 1983,pp. 11-19,4,Allan R. Liss, Inc.

OcanaQuero, J.et al., Biological effects of helium-neon irradiation on acrosome reaction in bull, Scisearch Journal of Photochemistry and Photobiology, vol. 40 No. 3, pp. 294-298 (1997).

Pangawkar, G. et al., Physical and biochemical characteristics of semen in relation to fertility of Holstein-Friesian bulls, Indian vet. Med.J. vol. 13: 21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Biology of Reproduction 37:1249-1258 (1987).

Parks, J. Processing and handling bull semen for artificial insemination—Don't add insult to injury!, Department of Animal Science Cornell University.

Partec, Taking flow cytometry to the next generation, Catalogue 2001-2002.

Perez-Pe, R.et al., Semen plasma proteins prevent cold shock membrane damage to ram spermatozoa, Theriogenology 56 (3) : 425-434, Aug. 1, 2001, PMID: 11516122 http.//www.ncbi.nlm.nih.gov/entrez/query.fcgi?CMD=search&DB=pubmed.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, voI. 56A Num.2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research an International Journal, vol. 95, No.3, Sep. 1983.

Piumi, F. et al., Specific cytogenetic labeling of bovine spermatozoa bearing X or Y chromosomes using florescent in situ hybridization (FISH), Genet, Sel. vol. 33: 89-98 (2001).

Polge, C., Low-temperature storage of mammalian spermatozoa, Unit of Reproductive Physiology and Biochemistry, Cambridge.

Edited by Bell-Prince, C., NFCR Newsletter, http://www.ls.lanl.gov/NFCR/newsletter-Oc98/oct98.html Jan. 6, 2004.

Rasul, Z.et al., Changes in motion characteristics, plasma membrane integrity, and acrosome morphology during cryopreservation of buffalo spermatozoa, Journal of Andrology, vol. 22 No.2, Mar. 4, 2001.

Rees, William A., et al,Betaine Can Eliminate the Base Pair Composition Dependence of DNA Melting; Biochemistry 1993, 32, pp. 137-144.

Rens, W.et al.,An X-Y paint set and sperm FISH protocol that can be used for validation of cattle sperm separation procedures, Journals of Reproduction and Fertility, 121: 541-546 (2001).

Reyes, C.et al., Characterization of Secretory Proteins from cultured Cauda Epididymal Cells that significantly sustain bovine sperm motility, Molecular Reproduction and Development 63: 500-509 (2002).

Rippel,N. et al., Transcervical insemination: Effects of variation in total sperm number/dose on fertility, 83rd Annual Fall Conference for Veterinarians, Oct. 2002.

Rizzo, W. et al.,Liposome-mediated transfer of simian virus 40 DNA and minichromosome into mammalian cells, J. Gen. Virol 64:911-919 (1983).

Ruch, F., Determination of DNA content by microfluorometry, Introduction to Quanitative Cytochemistry, pp. 281-294 (1966).

Saacke, R.et al., Semen Quality test and their relationship to fertility, 4th National Association of Animal Breeders, (1972).

Salisbury, G.W.,et al."Preservation of Bovine Spermatozoa in Yolk-Citrate Diluent and Field Results from its Use", Journal of Dairy Science, 1941, vol. 24(11),pp. 905-910.

Schroter, S.et al., The glycocalyx of the sperm surface, Human Reproduction Update: vol. 5, NO.4, pp. 302-313 (1999).

Schuster, T. et al., Isolation of motile spermatozoa from semen samples using microfluidics, Reproductive BioMedicine Online,vol. 7 No.1 75-81,www.rbmonline.com/Article/847, Apr. 16, 2003.

Seidel, George E. Jr. "What about sexed semen?" Hoard's Dairyman, The National Dairy Farm Magazine, May 10, 2001.

Sexing Technologies, Welcome to sexing Technologies, http://www.sexingtechnologies.com/ Dec. 11, 2003.

Shapiro, Howard M. M.D.,Building Flow Cytometers Chapter 9. Practical Flow Cytometry, second edition, Property of Washington University Medical Library.

Sharp, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 3, 2004.

Smith, P.et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytometry 40:280-291 (2000).

Stanger, J.et al., The Relationship between motility and the FITC-BSA binding Properties of Mouse epididymal spermatozoa, The Journal of Experimental Zoology 227: 323-327 (1983).

Stanic,P. et al.,Comparison of protective media and freezing techniques for cryopreservation of human semen, http://www.ncbi.nlm.nih.gov/entrez/query.fcgi?CMD=search&DB=pubmed , Jul. 11, 2000.

Stewart,R., Georgia Beef Challenge, Livestock Newsletter Jan.-Feb. 2002.

Takacs, T.et al.,Flow Cytometric determination of the sperm cell number in diluted bull semen samples by DNA staining method, Acta Biochim.Biophys.Hung. vol. 22 No.1, pp. 45-57 (1987).

Thurston,L. et al., Identification of Amplified restriction fragment length polymorphism markers linked to genes controlling boar sperm viability following cryopreservation, Biology of Reproduction 66: 545-554 (2002).

Tone,S.et al., A method of vital staining of mouse eggs using Hoechst dye, Department of Developmential Biology (1986).

Tubman,L.et al., Abstract:Normality of calves resulting from sexed sperm, http://www.cvmbs.colostate.edu/bms/abstract/ges12.html Mar. 16, 2004.

Tucker,K.et al., Sperm separation techniques:Comparison of gradient products, Proceedings 2ed International workshop for Embryologists: Troubleshooting activities in the ART lab. (2002).

Van Dilla, M.et al., Measurement of Mammalian Sperm Deoxyribonucleic acid by Flow Cytometry, The journal of Histochemistry and Cytochemistry vol. 25 Num.7 pp. 763-773 (1977).

Vazquez, J.et al., Nonsurgical Uterotubal Insemination in the Mare, Reproduction: Mare vol. 44 (1998).

Vishwanath,R.et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/an sci/extention/animal/news/april96/april1965.html Mar. 16, 2004.

Welch, G. et al., Sex preselection: Laboratory Validation of the sperm sex ratio of Flow sorted X and Y-sperm by sort reanal ysis for DNA, Theriogenology 52:1343-1352 (1999).

Welch, G. et al., Fluidic and optical modification to a facs IV for flow sorting of X&Y Chromosomes bearing sperm based on DNA, International Society for Analytical Cytology (1994).

Wiltshire, M. et al., A Novel Deep Red/ Low infrared fluorescent flow cytometric probe DRAQ5NO, for the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D. et al., Changes in sperm plasma membrane lipid diffusibility after hyperactivation during In vitro capacitation in the mouse, The Journal of Cell Biology, vol. 102: 1372-1377(1986).

Wolf, D. et al., Diffusion and regionalization in membranes of maturing ram spermatozoa, The Journal of Cell Biology, vol. 98:1678-1684 (1984).

XY Files, Issue 1 Jun. 1999.

XY, Inc., Sex selection Procedure, http://www.xyinc.com/sex select.html, Feb. 21, 2003.

XY Files, Issue 4 Aug. 2000.

XY Files, Issue 2 Oct. 1999.

XY Files, Issue 3 Mar. 2000.

XY Files, Issue 5 Mar. 2001.

XY Files, Issue 6 Mar. 2002.

Johnson, L.A., et al, 1996 Gender preselection in mammals. XX Beltsville Symposium in Agricultural Research Technolgys Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low Nos. Of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Parallel Chinese Application No. 03819362.0; Office Action dated Feb. 20, 2009.

Parallel Australian application No. 2003265471; Notice of Acceptance dated Jul. 22, 2009.

Parallel Chinese application No. 03819362.0, Office Action dated Feb. 20, 2009.

Parallel Chinese application No. 03819362.0, Notice of Decision to Grant dated Aug. 7, 2009.

Parallel Japanese application No. 2004-529536, Office action dated Apr. 21, 2009.

* cited by examiner

Fig 4
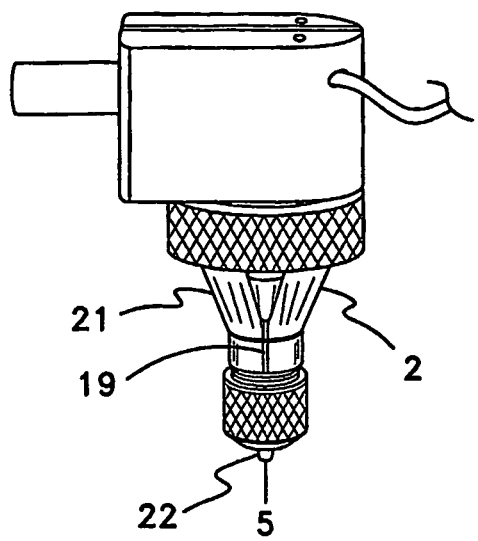
Fig. 4A
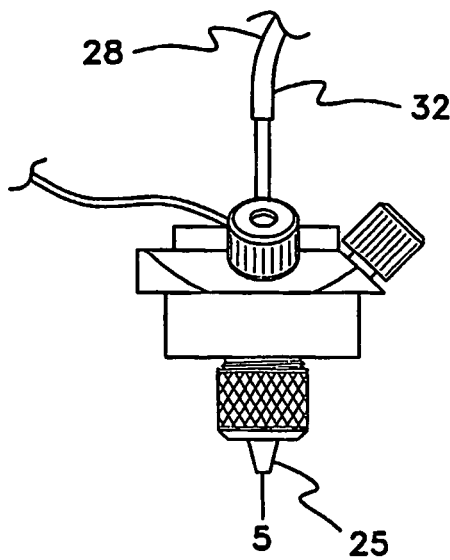
Fig. 4C
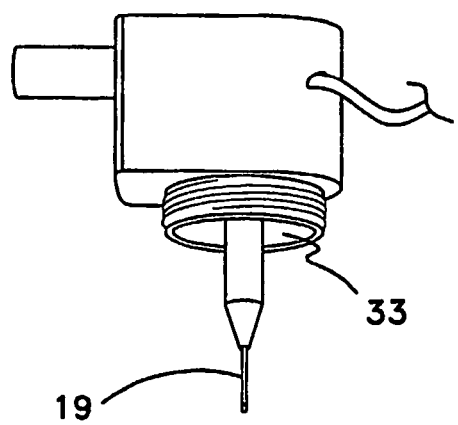
Fig. 4B
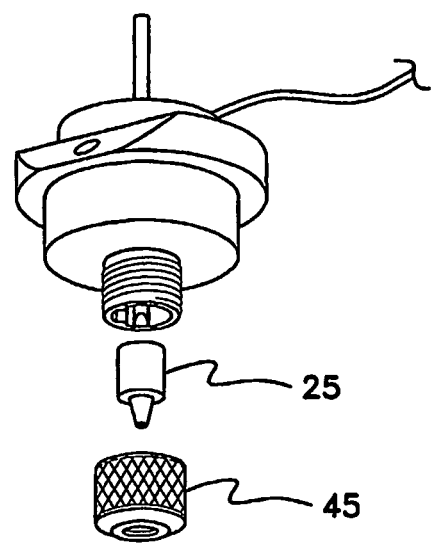
Fig. 4D

Fig 5
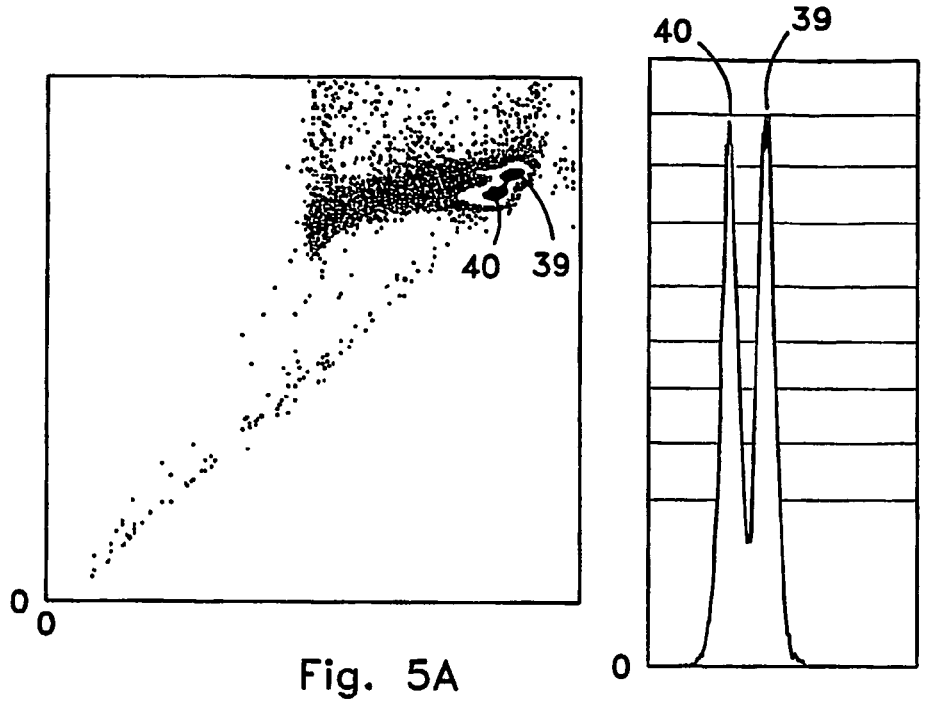
Fig. 5A
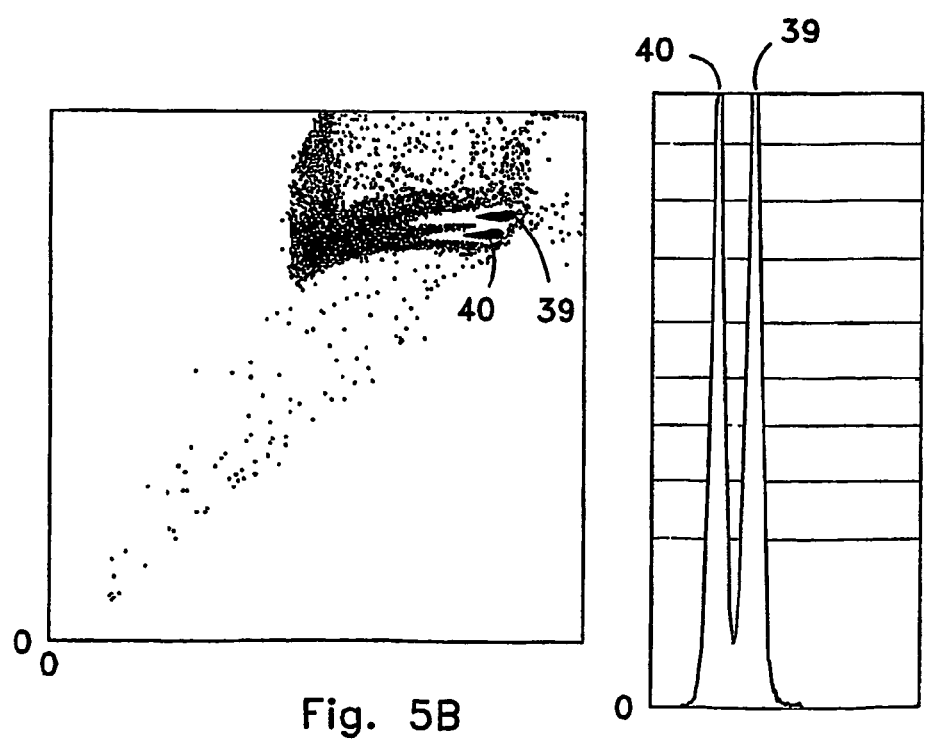
Fig. 5B

Fig 6
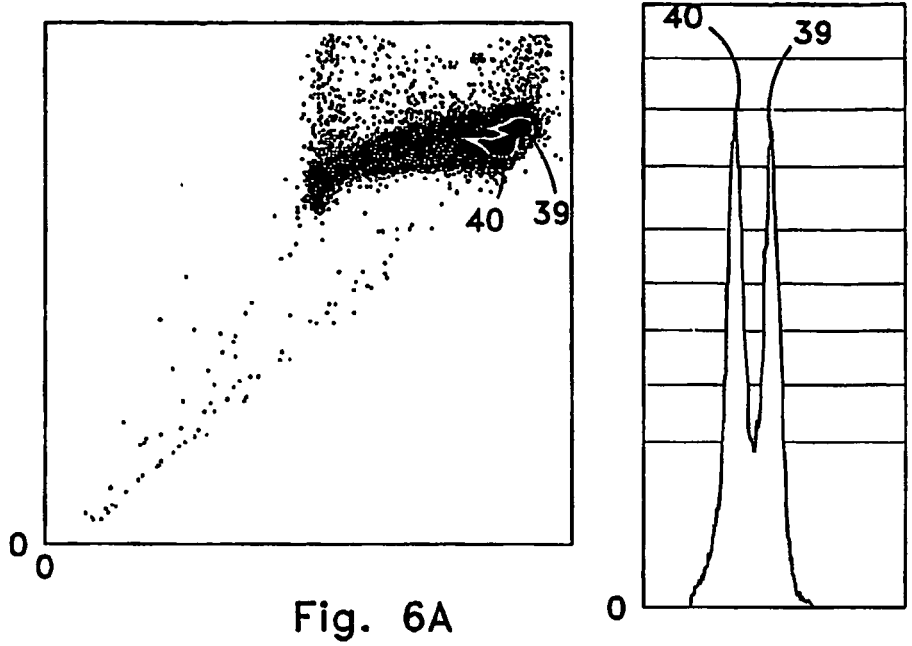
Fig. 6A
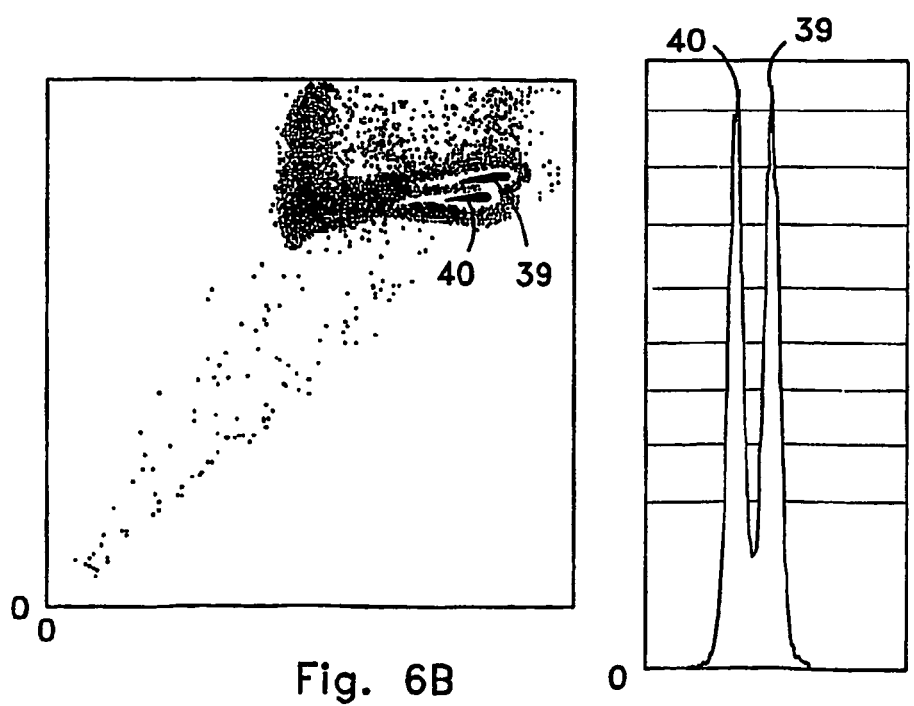
Fig. 6B

Fig 7
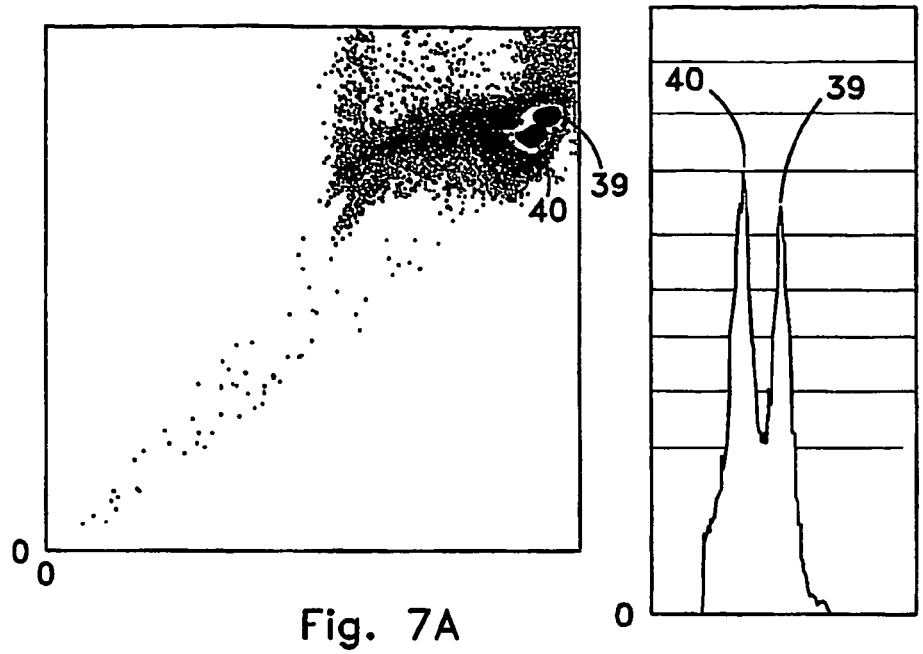
Fig. 7A
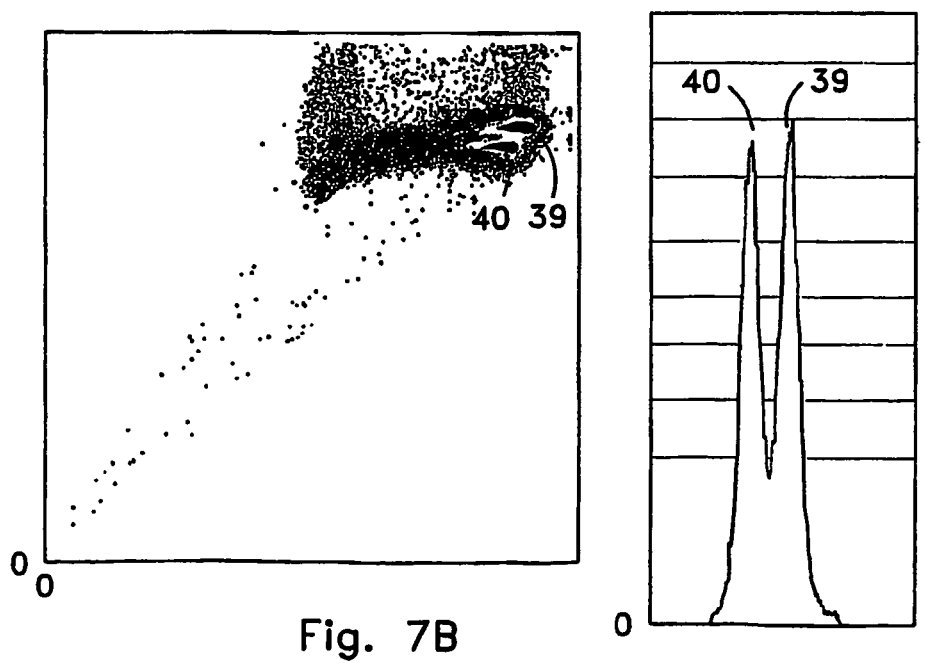
Fig. 7B

Fig 8
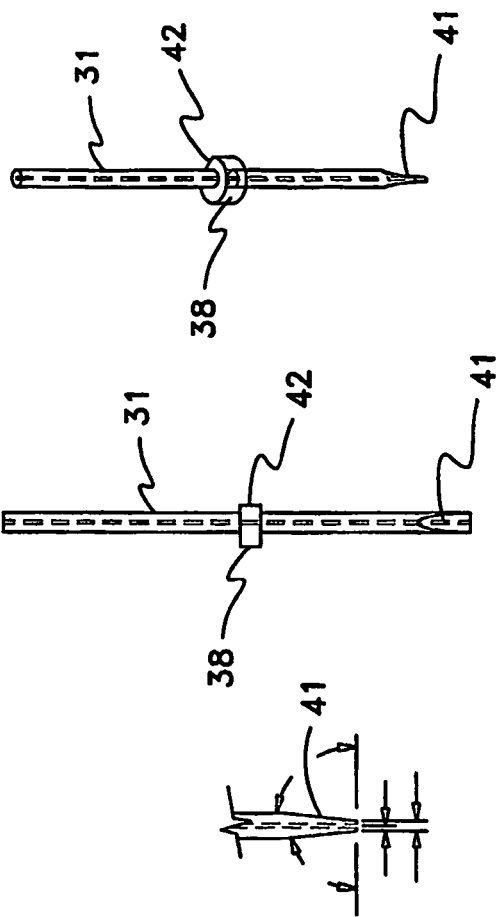
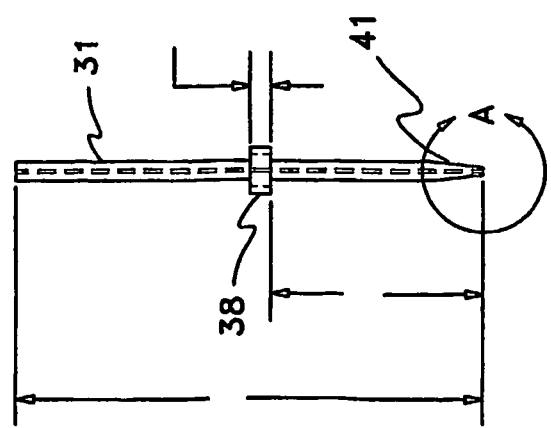

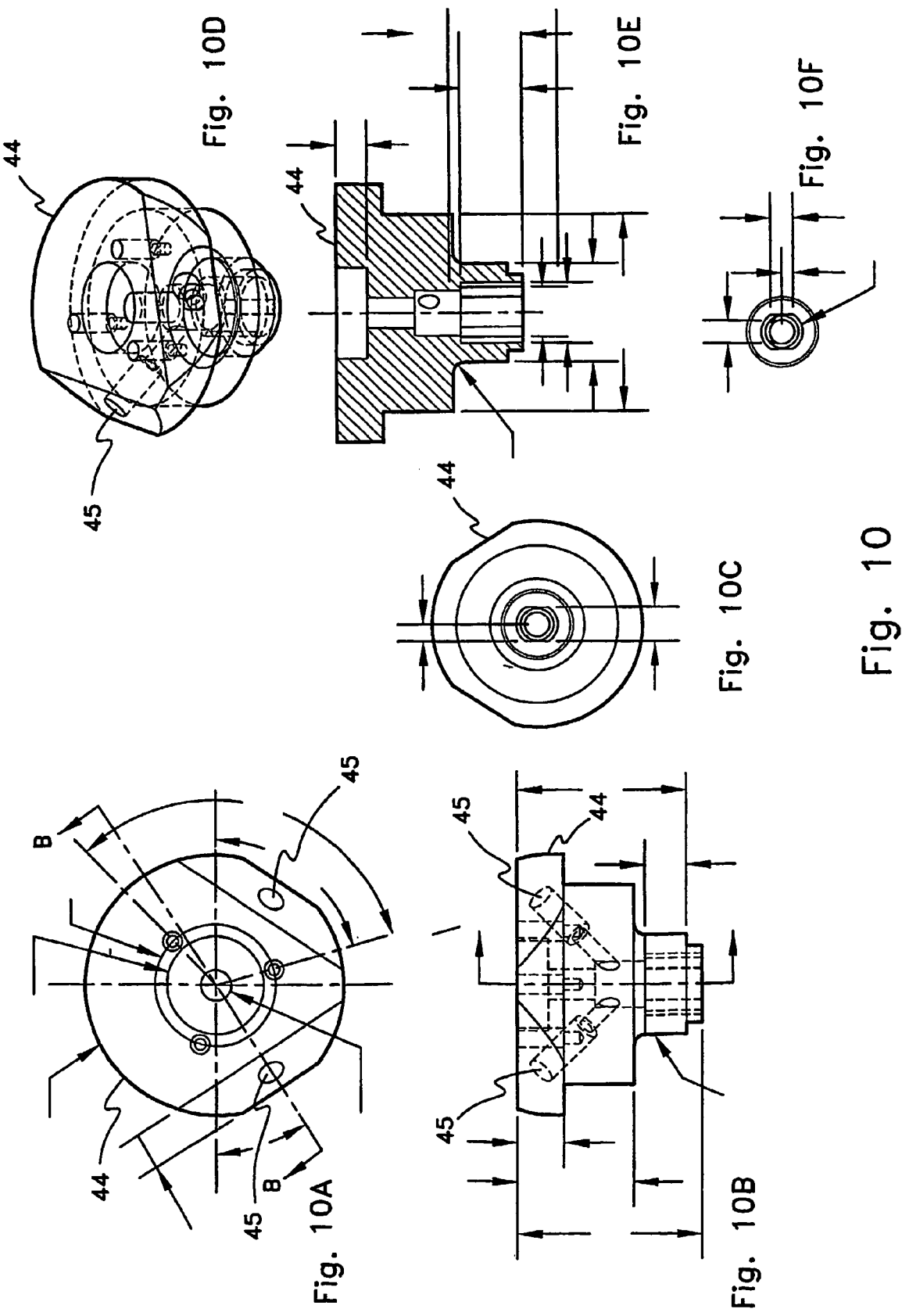

HIGH RESOLUTION FLOW CYTOMETER

This application is the United States National Stage of International Application No. PCT/US2003/025812, filed Aug. 15, 2003 which claims the benefit of U.S. Provisional Patent Application No. 60/404,279, filed Aug. 15, 2002, each hereby incorporated by reference herein.

I. TECHNICAL FIELD

High resolution differentiation and separation of particles based upon particle characteristics. Specifically, high resolution differentiation and separation of sperm cells into X-chromosome bearing and Y-chromosome bearing populations or increased homogeneity.

II. BACKGROUND

Effective preselection of sex has been accomplished in many species of mammal following the development of safe and reliable methods of separating sperm cells into enriched X chromosome bearing and Y chromosome bearing populations. Separation of X chromosome bearing sperm cells from Y chromosome bearing sperm cells can be accomplished as disclosed herein and as disclosed by various international patent applications, for example: WO 98/34094, WO 99/33956, WO 99/42810, WO 00/06193, WO 01/40765, WO 01/85913, WO 02/43486, WO 02/43574, each hereby incorporated by reference herein.

Now referring to FIGS. 1 and 2, a conventional technology flow cytometer provides a particle or cell source (1) that acts to establish or supply particles or cells (16) (which can be sperm cells or spermatozoa, sperm heads, commonly occurring blood cells such as leukocytes, lymphocytes, monocytes, neutrophils, basophils, macrophages, erythrocytes, platelets, or rare cell types such as fetal cells in circulation within maternal blood, cells which harbor viruses, cancer cells, and the like, as well as parts of cells such as organelles, mitochondria, individual chromosome, as well as man made particles such as beads or microspheres or nanospheres to which a biological component may be bound) that can be stained with at least one fluorochrome for analysis. The particles or cells (16) are introduced within a nozzle (2) in a manner such that the particles or cells (16) are introduced into a fluid stream or sheath fluid (3). The fluid stream (3) is usually supplied by some fluid source (4) so that as the particle or cell source (1) supplies the particles or cells (16) into the fluid (3) they are concurrently fed through the nozzle (2).

In this manner, the fluid stream (3) forms a fluid environment for the particles or cells (16). Since the various fluids are provided to the flow cytometer at some pressure, they exit out of nozzle (2) at a nozzle orifice (5). By providing some type of oscillator (6) which may be very precisely controlled through an oscillator control (7), pressure waves may be established within the nozzle (2) and transmitted to the fluid stream (3) exiting the nozzle (2) at nozzle orifice (5). Since the oscillator (6) acts upon the sheath fluid (3), the fluid stream (8) formed below the nozzle orifice (5) eventually and regularly forms drops (9). Since particles or cells (16) are surrounded by the fluid stream (8) formed below the nozzle orifice, the drops (9) may entrain within them individually isolated particles or cells (16).

Since the drops (9) can entrain individual particles or cells (16), a flow cytometer can be used to separate such particles or cells (16) based upon particle or cell characteristics. This is accomplished through a particle or cell sensing system (10).

The particle or cell sensing system involves at least some type of detector or sensor (11) that responds to the particles or cells (16) contained within fluid stream (8). The particle or cell sensing system (10) may cause an action depending upon the relative presence or relative absence of a characteristic, such as fluorochrome bound to the particle or cell or component thereof, such as DNA or lipids, or mitochondria, or organelles within the cell, that may be excited by an irradiation source such as a laser (12) generating an irradiation beam to which the particle or cell (16) can be responsive.

While each type of particle, cell, or component thereof may be stained with at least one type of fluorochrome, different amounts of fluorochrome(s) bind to each individual particle or cell (16) based on the number of binding sites available to the particular type of fluorochrome used. With respect to spermatozoa, as but one example, the availability of binding sites for Hoechst 33342 stain is dependant upon the amount of DNA contained within each spermatozoa. Because X-chromosome bearing spermatozoa contain more DNA than Y-chromosome bearing spermatozoa, the X-chromosome bearing spermatozoa of a species of mammal can bind a greater amount of fluorochrome than the corresponding Y-chromosome bearing spermatozoa of the same species of mammal. Thus, by measuring the fluorescence emitted by the bound fluorochrome upon excitation, it can be possible to differentiate between X-bearing spermatozoa and Y-bearing spermatozoa.

In order to achieve separation and isolation based upon particle or cell characteristics, emitted light can be received by sensor (11) and fed to some type of separation discrimination system (13) coupled to a droplet charger which differentially charges each droplet (9) based upon the characteristics of the particle or cell (16) contained within that droplet (9). In this manner the separation discrimination system (13) acts to permit the electrostatic deflection plates (14) to deflect drops (9) based on whether or not they contain the appropriate particle or cell (16).

As a result, a flow cytometer acts to separate individual particles or cells (16) entrained in drops (9) by causing them to be directed to one or more collection containers (15). For example, when the separation discrimination system (13) differentiates sperm cells based upon the relative amounts of DNA contained by X-chromosome bearing spermatozoa and Y-chromosome bearing spermatozoa, the droplets entraining X-chromosome bearing spermatozoa can be charged positively and thus deflect in one direction, while the droplets entraining Y-chromosome bearing spermatozoa can be charged negatively and thus deflect the other way, and the waste stream (that is droplets that do not entrain a particle or cell (16) or entrain undesired or unsortable cells) can be left uncharged and thus may be collected in an undeflected stream. Numerous deflection trajectories can be established and collected simultaneously with some conventional flow cytometers.

Even though conventional flow cytometers for the separation of cells or particles have been improved over the past several years significant problems still remain with respect to the resolving capacity of convention flow cytometers.

A significant problem with conventional flow cytometer technology as shown by FIG. 1 may be that the fluid source (4) along with the associated fluid source conduit(s) (23) introduces fluid (3) into the nozzle (2) substantially perpendicular to the flow of the fluid (3) within the nozzle (2). These two directions of flow can interrupt, distort, or delay formation of laminar flow within the nozzle (2). Certain particles or cells (16), being large in comparison to the molecules of the fluid stream, and particularly in cases where the positioning, orientation, and inter-particle distribution is critical to accurate analysis of individual particles or cells (16), and correct entrainment of individual particles or cells (16) into individual drops (9) is required, are strongly influenced by fluid movement which may be turbulent, and therefore maintaining laminar flow is an important aspect, which has been overlooked in the design of conventional flow cytometer technology. It is also noteworthy that the oscillator (6) which serves the primary function of providing pressure waves to allow the formation of individual drops (9), will also provide standing waves of pressure within the nozzle (2) which will influence the laminar flow characteristics, especially as improper nozzle design can lead to harmonic divergences such as pressure beats or sub-oscillations.

A second significant problem with conventional flow cytometer technology as shown by FIG. 1 may be that the cell source conduit (17) between the cell source (1) and the nozzle (2) is not straight. A substantial bend in the cell source conduit (17) can result in a change in fluid pressure in response to the bend in the cell source conduit or can create fluid streams having areal cross sections that exhibit disparate stream velocity. This problem can be exacerbated by cells or debris aggregating at the bend(s) in the cell source conduit (17).

A third significant problem with conventional flow cytometer technology as shown by FIG. 1 may be that the cell source conduit (17) is too long. Conventional flow cytometer cell source conduit (17) from the cell source (1) to the injection point (18) of particles or cells into the fluid stream can be greater than four inches in length. Conventional length cell source conduit (17) can cause cells to settle or aggregate in, or flow through, the cell source conduit in a manner that increases turbulent flow, and therefore decreases apparent resolution of cell populations.

A fourth significant problem with conventional flow cytometer technology as shown by FIG. 1 may be that the cell source conduit (17) and in particular the particle injector (19) portion of the cell source conduit may not be individually replaceable. As such, a failure, or reduced performance, of the cell source conduit (17) or the particle. injector (19) portion can result in the necessity to replace the entire nozzle (2) and the cell source conduit (17) along with any other component of the flow cytometer inseparably joined to the nozzle (2).

A fifth significant problem with conventional flow cytometer technology can be that there may be a connector (20) mounted to the entry end of the particle injector (19) portion of the cell source conduit (17) to couple the injector portion (19) with the cell source fluid conduit (17). Even zero-dead volume connectors or couplers can introduce sufficient deformation or non-concentricity to the cell source conduit interior surface to allow particles or debris to adhere, cling, attach, or otherwise become immobilized at the location of the connector (20) resulting in potential cross contamination between sample populations transferred in the cell source fluid stream, or causing restrictions or otherwise altering the configuration of the cell source fluid path.

A sixth significant problem with convention flow cytometer technology can be that the interior surfaces of the cell source conduit (17) or the interior surfaces of the injector (19) portion of the cell source conduit (17) are sufficiently rough or uneven to reduce apparent resolution of mixed populations of cells or particles. One aspect of this problem can be that surface features that result in the rough or uneven surface can on occasion break away from the cell source conduit interior surface and can become lodged in the flow path. In some cases, restriction or occlusion of the cell source conduit (17) can result. Another aspect of this problem can be that particles interact with the rough or uneven features of the cell source conduit to create asymmetries in the velocity of the fluid stream, which can introduce sheer forces or turbulent flow properties that decrease apparent resolution of cell populations.

A seventh significant problem with conventional flow cytometry technology can be that areal cross sections of the nozzle (2) can be too large. The larger the area of the cross section of the nozzle (2), the greater the area on which bubbles or debris or particles (16) can attach and interfere with the fluid dynamics within the nozzle assembly, and the greater the complexity of standing pressure waves and sub-harmonic pressure waves which may be stabilized in the nozzle (2).

An eight significant problem with conventional flow cytometery may be that the body of the nozzle (2) comprises a first nozzle body element (21) and a second nozzle body element (22). This can create an interior surface of the nozzle having sufficient distortion or roughness to disrupt or diminish the laminar flow of the fluid stream which can translate into reduced resolving capacity of conventional flow cytometer(s), or if the two fabrication materials of a first nozzle body element (21) and a second nozzle body element (22) have different elasticities, they may each deliver pressure waves from the oscillator (6) with different sub-harmonic characteristics, which may tend to distort laminar flow in the critical area of the particle flow path just prior to exiting the nozzle (2) at the orifice (5).

A ninth significant problem in the conventional flow cytometry technology relates to the difficulty in accurate measurement of DNA in particles or cells, such as live mammalian sperm, which bind different amounts of fluorochrome based on known differences in DNA content, and yet have large coefficients of variation which obscure the measurement For example, as shown by Johnson et al., Theriogenology, Vol. 52, No. 8, 1326 (1999) the effect of the size of an X chromosome on total DNA content of a live sperm cell in comparison to the effect of the Y chromosome size on the total DNA of a live sperm cell is determined by the differences between the sizes of an X and a Y chromosome in a specific mammalian species, as well as the actual amount of DNA (numbers and sizes of all other chromosomes). And specifically (X-Y)/X of: 2.8% in humans, 3.0% in rabbits, 3.6% in boars (pig), 3.7% in stallion (horse), 3.8% in bull (cattle), 3.9% in dog, 4.2% in ram (sheep), and as much as 7.5% in chinchilla. Welch et al. show, however, that the coefficient of variation (CV) in the analysis of sperm by conventional methods is considered good vat 0.9% and can even be as high as 1.97%. Welch et al., Theriogenology, Vol. 52, No. 8, 1348 (1999) Thus, especially for species such as humans with very low (X-Y)/X values of 2.8%, it is critical to reduce the CV to lower than 1%, and preferably to as close to zero as possible. The definition of resolution, as used in the description of the instant invention, refers to the capability of the instrument in resolving of sperm into two populations based on the proximity of the measured value from each single sperm to a known value, with the primary negative determinant being a high CV for the population being analyzed.

The instant invention addresses the variety of problems associated with reduced resolution of conventional flow cytometer instruments in separating flow separable particles or cells (16), cells, and specifically sperm cells into enriched populations based upon particle characteristics, or in the context of sperm cells into enriched X-chromosome bearing and Y-chromosome bearing populations.

III. DISCLOSURE OF INVENTION

Accordingly, the broad object of the invention can be to provide an increased resolution flow cytometer which can afford increased homogeneity of isolated populations differentiated by one or more particle characteristics.

A first aspect of this object of the invention can be to introduce fluids from the fluid source (4) the into the nozzle (2) in a manner that reduces disruption, turbulence, distortion, or delay of formation the laminar flow of the fluid stream (3) within the nozzle (2) or establishing a laminer flow with the core stream containing particles or cells (16) introduced into the nozzle at the injection point (18).

A second aspect of this object of the invention can be to provide a cell source fluid stream between the cell source (1) and injection point that maintains a substantially constant areal velocity with respect to a cross section of the cell source fluid stream within the cell source conduit (17), or that substantially eliminates changes in velocity of the cell source fluid stream due to curvature, deformation, or bends in the cell source, or reduces impediments, obstructions, or particle aggregation or collect areas within the cell source conduit (17).

A third aspect of this object of the invention can be to provide an adjustable cell source fluid stream configuration that provides with respect to a particular type of particle or the type of particle differentiation characteristic, a cell source fluid stream volume that maintains consistency with respect to the flow of particles (16) from the cell source (1) to the injector point (18).

A fourth aspect of this object of the invention can be to provide an adjustable coaxial fluid stream that provides with respect to a particular type of particle, or with respect to a particular of type of particle differentiation characteristic, a core stream containing particles (16) within the fluid stream (8) formed below the nozzle orifice (5) that has greater consistency.

A fifth aspect of this object of the invention can be to provide a particle injector portion (31) of cell source conduit (28) that is replaceable.

A sixth aspect of this object of the invention can be to eliminate the connector (20) mounted to the entry end of the injector (19) portion of the cell source conduit (17).

A seventh aspect of this object of the invention can be to eliminate or substantially reduce the roughness or unevenness of the interior walls of the cell source conduit (17.

An eighth aspect of this object of the invention can be to provide a continuously integral one-piece nozzle to substantially eliminate or reduce non-concentricity of interior circular areal cross sections of the nozzle, or substantially eliminate or reduce deformations to the interior surface of the nozzle.

Another significant object of the invention can be to provide devices or methods of separating sperm cells that can maintain greater viability of mamalian sperm cells throughout a flow-sorting process.

Naturally, further significant objects of the invention are made clear in the proceeding description and drawings.

IV. BRIEF DESCRIPTION OF THE DRAWINGS

FIG. 4 provides a comparison of a conventional flow cytometer nozzle assembly (FIG. 4a) and the injector portion of conventional flow cytometer (FIG. 4b) with the corresponding resolution enhanced flow cytometer nozzle assembly invention (FIG. 4c) and the resolution enhanced injector portion of the enhanced resolution flow cytometer invention (FIG. 4d).

FIG. 5 provides a comparison of the resolution of a bovine sperm nuclei sample using conventional flow cytometer technology (FIG. 5a) and resolution of the same bovine sperm nuclei sample using the enhanced resolution flow cytometer invention FIG. 5b) each at 25,000 events per second.

FIG. 6 provides a comparison of the resolution of a bovine sperm nuclei sample using conventional flow cytometer technology (FIG. 6a) performed at 50,000 events per second and resolution of the same bovine sperm nuclei sample using the enhanced resolution flow cytometer invention FIG. 6b) performed at 60,000 events per second.

FIG. 7 provides a comparison of the resolution of a bovine sperm nuclei sample using conventional flow cytometer technology (FIG. 7a) performed at 100,000 events per second and resolution of the same bovine sperm nuclei sample using the enhanced resolution flow cytometer invention (FIG. 7b) performed at 110,000 events per second.

FIG. 8 shows a particular embodiment of the particle injector invention.

Figure 9:
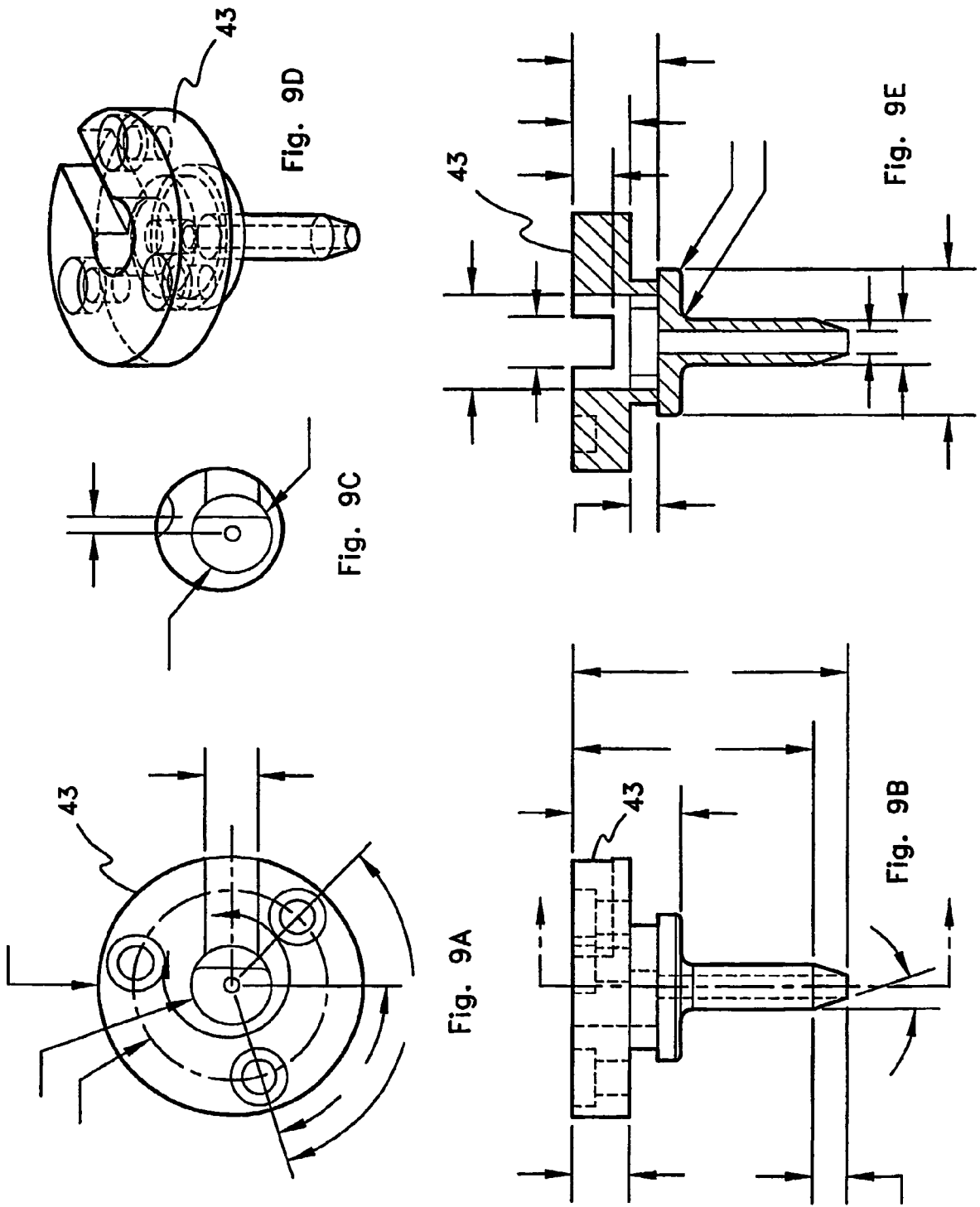

FIG. 9 shows a particular embodiment of an inner nozzle body invention.

FIG. 10 shows a particular embodiment of an outer nozzle body invention.

FIG. 11 provides cross section B-B of the particular embodiment of the outer nozzle invention shown in FIG. 10.

V. MODE(S) FOR CARRYING OUT THE INVENTION

The invention involves a high resolution flow cytometer that can increase resolving power to separate mixed populations of cells, sperm cells, or particles from each other based upon various cell or particle characteristics individually or in combination.

As such, while particular examples of the invention are provided that describe the invention in the context of separating sperm cells, or separating bovine or equine intact live sperm cells, it should be understood that the enhanced resolution technologies described can have application with respect to separation of various types of flow separable particles, including, but not limited to, cells, spermatozoa, or sperm nuclei, collected, handled, or stored in a variety of ways.

X-chromosome bearing and Y-chromosome bearing populations of spermatozoa should further be understood to encompass enriched populations of flow separated or sorted spermatozoa obtained from a male of a species of mammal including, but not limited to, spermatozoa from humans; as well as other mammals such as bovids, equids, cervids, ovids, canids, felids, goats, swine, or camels; as well as marine mammals, such as cetaceans (various species of whales or porpoises); and specifically including endangered mammalian species; and particular individuals of a species that may be zoological specimen(s), rare or prize specimen(s), or a specimen of a species of mammal that provides semen for use in animal husbandry, herd management systems, artificial insemination protocols, cryogenic storage, or for example a species of mammal listed by Wilson, D. E. and Reeder, D. M., *Mammal Species of the World*, Smithsonian Institution Press, (1993), hereby incorporated by reference herein.

This list of animals is intended to be exemplary of the great variety of mammals from which spermatozoa can be obtained or which can be flow sorted with the enhanced resolution flow cytometer invention described herein and it is not intended that the high resolution or enhanced resolution aspects of the invention be limited to the analysis or the flow separation of any particular type of particle or the spermatozoa from any particular species of mammals or individual mammal.

Cells, spermatozoa, or particles obtained using the enhanced resolution flow cytometry invention described herein can be incorporated into various applications or products including but not limited to artificial insemination protocols or as part of commercial business methods such as those as described in Patent Cooperation Treaty Application Nos. PCT/US01/18879 or PCT/US99/17165; or be used with low dose insemination protocols as described in Patent Cooperation Treaty Application No. PCT/US98/27909, or used with in-vitro fertilization of oocytes from animals, including humans, as described in Patent Cooperation Treaty Application No. PCT/US01/45237, each of the above-mentioned applications or documents hereby incorporated by reference.

The use of the term purity should be understood to be the percent of the isolated spermatozoa population bearing a particular differentiating characteristic or desired combination of characteristics. For example, where a population of spermatozoa are separated based upon bearing an X-chromosome as opposed to a Y-chromosome, a X-chromosome bearing population having 90% purity comprises a population of spermatozoa of which 90% of the individual spermatozoa bear an X-chromosome while 10% of such population of spermatozoa may bear a Y-chromosome. As such, purity with respect to X-chromosome bearing populations or Y-chromosome bearing populations of spermatozoa generated in accordance with the invention can comprise a purity greater than achieved with convention flow separation devices or can comprise a purity of between about 70% to about 99%, or can be selected from the group consisting of between 90% to about 100%, between about 91% to about 100%, between about 92% to about 100%, between about 93% to about 100%, between about 94% to about 100%, between about 95% to about 100%, between about 96% to about 100%, between about 97% to about 100%, between about 98% to about 100%, between about 99% to about 100%.

Importantly, while this description includes numerous embodiments of the invention some of which may include isolated X-chromosome and Y-chromosome bearing populations of spermatozoa, and while the description further discloses specific aspects of enhanced resolution spermatozoa separation devices or methods of how to enhance resolution of mixed populations of spermatozoa, the basic concepts of the invention should be understood to be applicable to other types of particles or events having similar or different particle differentiation characteristics or event differentiation characteristics. It should be understood that the invention can be applicable to a variety of circumstances including those in which enhanced resolving capacity of small differences in photogenerated signal may be necessary.

Moreover, while this disclosure provides descriptions of embodiments of apparatus and methods for flow separation of X-chromosome bearing spermatozoa from Y-chromosome bearing spermatozoa, the description of these embodiments of the invention is not meant to reduce the scope of the invention to only flow separation of spermatozoa or only to high or enhanced resolution flow cytometer spermatozoa separation systems but rather these examples are intended to exemplify the basic concepts of the invention in a practical manner so that they may be applied to the wide variety of particles or applications.

Figures 3, 3A, 3B, 3C, 3D:
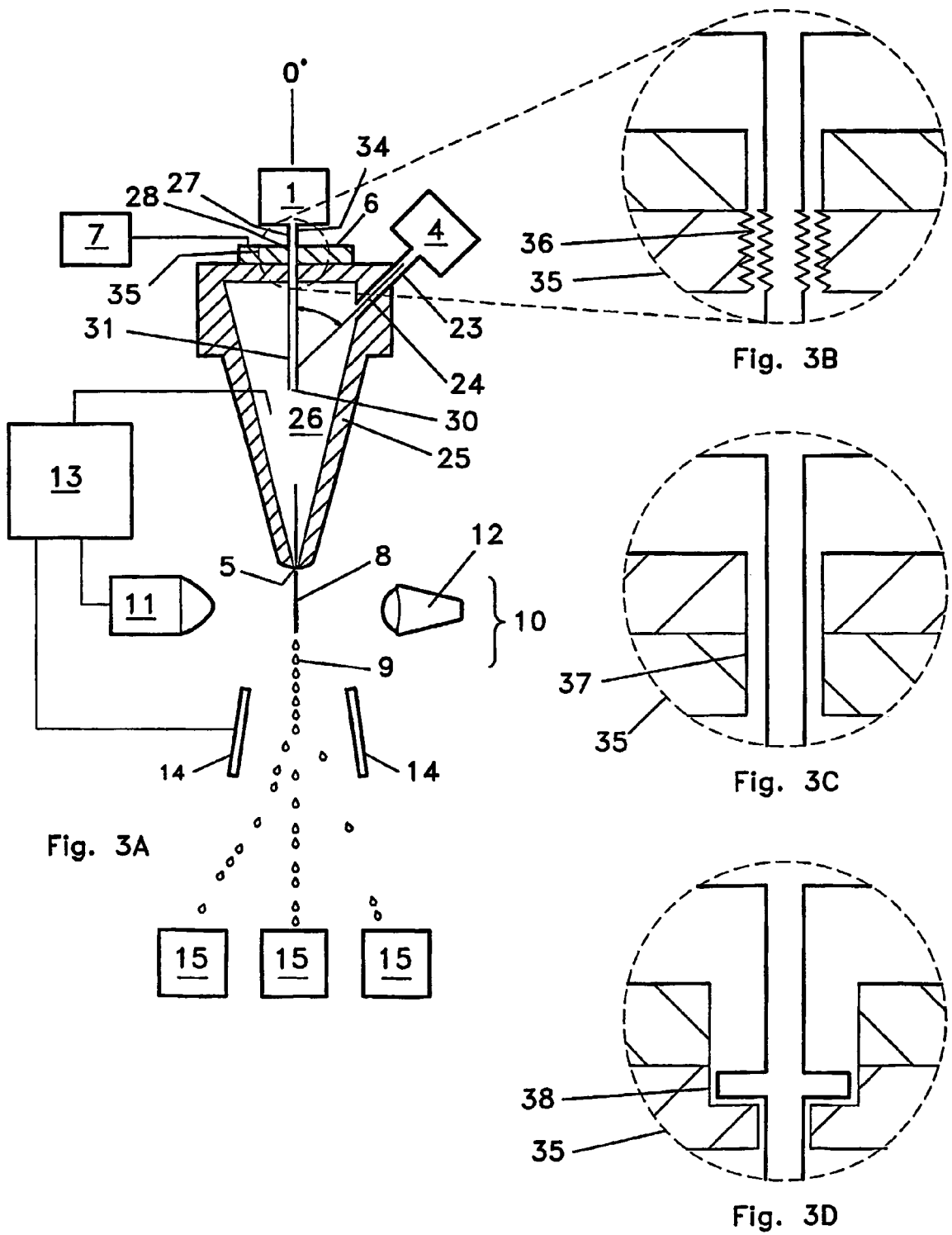
FIG. 3 shows a particular embodiment of the enhanced resolution flow cytometer invention.

Now referring primarily to FIG. 3, the invention can comprise at least one fluid source conduit (23) that introduces a fluid source stream (24) into the enhanced resolution nozzle (25) at an angle relative to fluid stream (26) flow within the nozzle (25) that enhances particle resolution by the cell sensing system (13). The angle of introduction can vary depending on the type of particle populations being differentiated. With respect to some embodiments of the invention, the fluid source conduit (23) can introduce the fluid source stream (24) at an angle between about zero degrees to about 45 degrees with respect to the central longitudinal axis of the enhanced resolution nozzle (25). With respect to certain embodiments of the invention, a plurality of fluid source conduits (23) can introduce a plurality of fluid source streams (24) into the enhanced resolution nozzle (25).

Again referring primarily to FIG. 3, the invention can further comprise a symmetrical velocity cell source fluid stream (27) within the cell source conduit (28). A symmetrical velocity cell source fluid stream provides cell source fluid stream (27) having a velocity that achieves substantially symmetry across the perpendicular cross section of the cell source fluid stream (27) which can include the anticipated symmetry associated with the reduction in velocity near or at the interior surface of the cell source conduit (28), but avoids or reduces asymmetries of velocity across a perpendicular cross section of the cell source fluid stream (27). To establish this symmetry in velocity of the cell source fluid stream (27), certain embodiments of the invention can utilize a substantially linear cell source conduit (28). A linear cell source conduit (28) presents a linear flow path or more linear flow path than conventional technology to the cell source fluid stream (27) without any substantial curvature, bends, or turns that may upon negotiation by the cell source fluid stream (27) require a portion of the cell source fluid stream (27) to reduce velocity or a portion of the stream to increase velocity. As such, as compared to conventional technology the symmetrical velocity cell source fluid stream (27) provides a solution to the problems described below with conventional type cell source fluid streams (29), as shown in FIG. 1.

Figure 1:
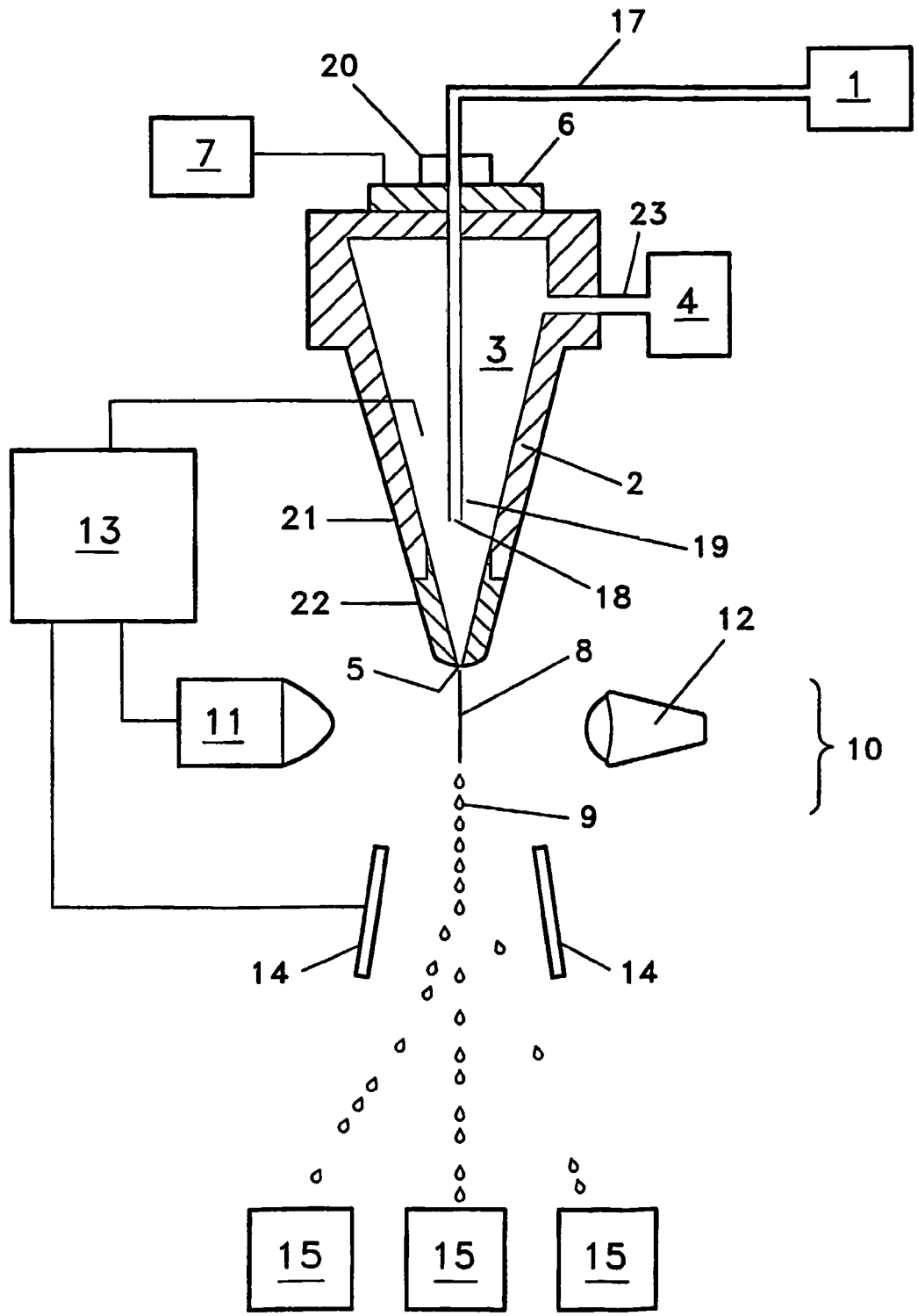
FIG. 1 shows a schematic representation of conventional flow cytometer technology.
Figure 2:
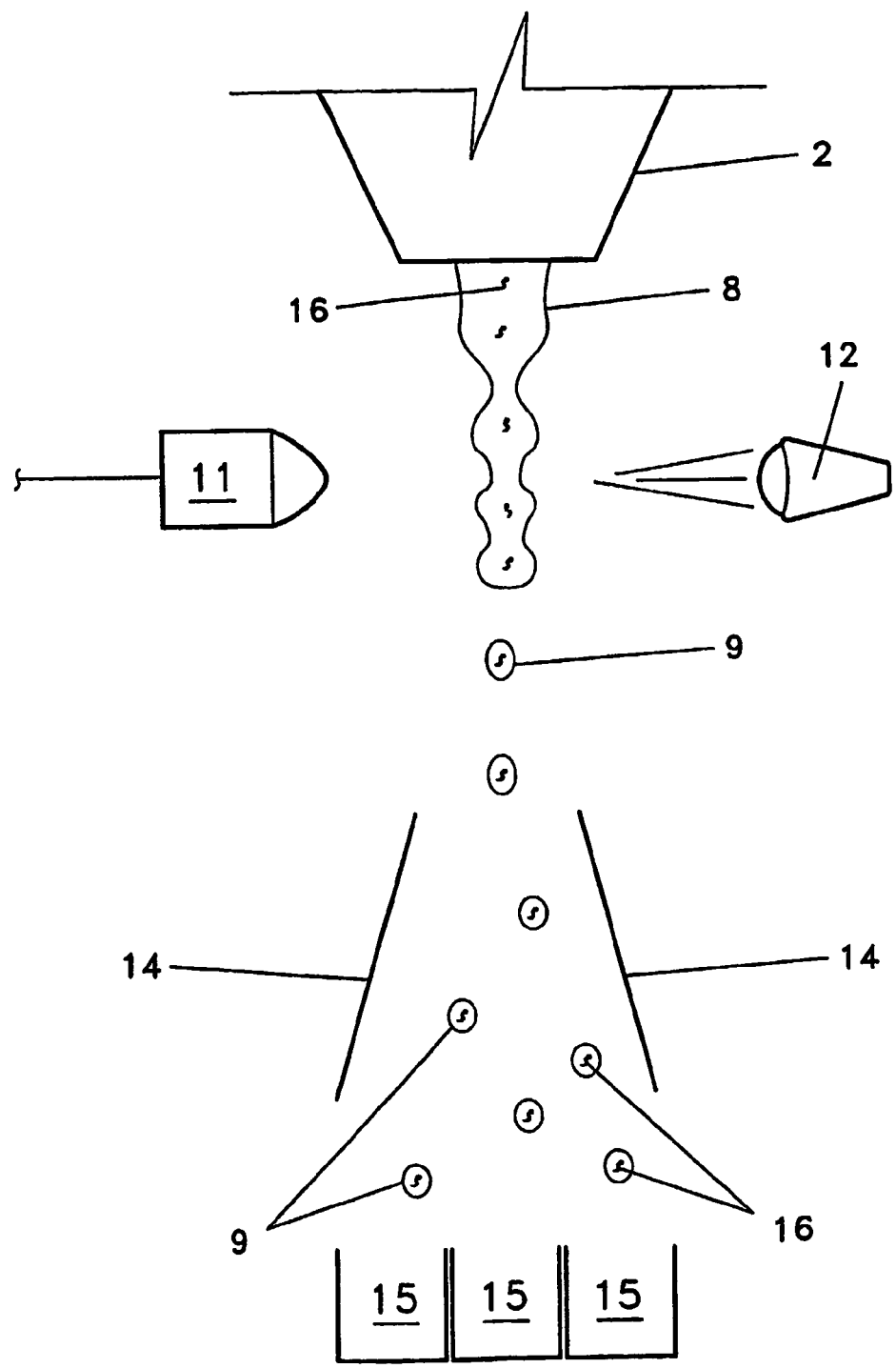
FIG. 2 shows a schematic representation of conventional flow cytometer technology.

Now referring to the convention technology illustrated by FIG. 1, when stream velocity is not symmetrical, cells introduced into the cell source fluid stream (29) can travel at different rates respectively and the initial distribution of the particles by the cell source (1) into the conventional cell source fluid stream (27) can be effected resulting in a substantially different distribution of cells presented at the injection point (18) that can effect the apparent resolution of particle populations.

Of particular problem with conventional technology, the cell source conduit (17) can have, for example, a 90° bend necessitating the conventional cell source fluid stream (29) to respond to a small radius curvature or bend. At the turn, cell source fluid stream (29) velocity may abruptly drop across the entire cross sectional area of the cell source fluid stream (29) or a portion thereof. This reduction in cell source stream (29) velocity may with respect to the smaller interior radius of the bend be substantially reduced with respect to the velocity of the stream adjacent to the larger exterior radius. This can in some circumstances result in particles that accumulate or aggregate at the curvature or bend in the cell source conduit (17) that can further exacerbate asymmetry in the cell source fluid stream (29) and further interfere with the distribution of particle delivery at the injection point (18). In some instances, the particles may interrupt flow of the cell source fluid stream (29) in part or all together resulting in failure of the flow separation events entirely.

Some embodiments of the invention can include independently or in combination with other aspects of the invention a limited resistance interface surface between the cell source fluid stream (27) and the interior of cell source conduit (28). The limited resistance interface surface with respect to materials such as plastic or metal can comprise a polished or smoothed interior surface of the cell source conduit (28). The interior surface(s) can be polished or smoothed until the observed resolution increase reaches a maximum, or desired amount. Alternately limited resistance or distortion of the interface surface can be accomplished by substitution of materials that are used to manufacture the cell source conduit (28). For example, glass tube or Teflon® tube, can be substituted for metal or other types of plastic tube. A limited resistance cell source conduit (28) can be further accomplished by chemical treatment of the interior surface of the cell source conduit (28). In these embodiments of the invention, plastics or glass for example can be silanized, while metals can be further passified by acid wash.

Again referring primarily to FIG. 3, embodiments of the invention can include an cell source fluid stream (27) having adjusted coaxial fluid stream characteristics. Because resolution of particles can be dependent upon fluid stream characteristics generated by operating parameters such as temperature, stream velocity, stream pressure, configuration of conduits in which the fluid stream flows, injection point of particles in the stream, type of particle injected into the stream, or the like, it can be important to control stream characteristics to achieve, maintain, or enhance resolution of particle populations. As such, the diameter or length of the cell source conduit (28), and location of the injection point (30) within the nozzle (25) of the cell source fluid stream (27) can each, or in combination, effect resolution of particle populations.

As to some embodiments of the invention particle injector (31) can have a built in selectably variable adjustment element (35) which allows adjustment or alteration of the distance between the nozzle orifice (5) and the location in the fluid stream (26) at which the particle injector (31) entrains particles (16) delivered from cell source (1). Selectably variable adjustment of the particle injector (31) allows alteration of fluid stream characteristics in compensation for a change of operation conditions from a first set of operating conditions to a second set of operating conditions whether the change in operation conditions comprises a change in sheath fluid, species of sperm cell, temperature, fluid stream pressure, fluid stream temperature, or otherwise. Importantly, by adjusting the distance between the particle injector (31) and the nozzle orifice (5) increased resolution based on a characteristic of cells can be achieved. With respect to sperm cells, increased resolution of sperm cells separated based upon bearing an X-chromosome or a Y-chromosome can be achieved utilizing the invention, as shown by FIGS. 5-7.

Selectable variable adjustment of the particle injector (31) to allow adjustment of the injection point (30) can be accomplished in a variety of ways. First, as shown by FIG. 3*b*, a pair of mated spiral threads (36) engaged between the particle injector (31) and the nozzle body (25) can provide rotational adjustment of the particle injector (31) to alter the location of the injection point (30). Second, as shown by FIG. 3*c*, adjustable engagement can be provided between the particle injector (31) and the nozzle body (25) by providing slidable engagement (37). Third, as shown by FIGS. 3, 4*d*, and 8 a plurality of interchangeable particle injectors (31) can have alternate lengths established by at keyed stop (38) mated with the nozzle body (25).

Now referring primarily to FIGS. 3 and 4, the invention can further comprise a single piece nozzle (25) (FIG. 4*d*). Unlike the nozzle (2) shown in FIGS. 1 and 4*a*, the instant invention can eliminate non-concentricity that can occur during mating of two or more discrete nozzle elements, such as the first nozzle element (21) and the second nozzle element (22) as shown in FIGS. 1 and 4*b*.

Again referring primarily to FIGS. 3 and 4, the invention can further comprise a compression sleeve coupler (32) to replace the connector (20) included in conventional technology. An embodiment of the compression sleeve coupler (32) can comprise the terminal end of the cell source conduit (28) which has sufficient resiliently elastic properties to couple with the particle injector (31) tube. This embodiment of the invention can comprise a cell source conduit comprising Silastic® or other material having Silastic® like properties, or a cell source conduit (28) have sufficient elastic properties, such as Teflon® or resiliently elastic properties such as Tygon® to conform to the exterior surface of the particle injector (31) tube.

Now referring primarily to FIGS. 4*a* through 4*d*, a conventional nozzle assembly (FIGS. 4*a* and 4*b*) are shown in comparison with the invention (FIGS. 4*c* and 4*d*). As can be understood by the comparison of FIG. 1 and FIG. 3 and FIG. 4*b* and FIG. 4*d*, the conventional technology necessitates use of a longer flow path between the cell source (1) and the injection point (18)(see longer particle injector tube FIG. 4*b*) and a longer fluid stream path (3) between the fluid source and the injection point (18). The longer flow paths utilized by the conventional technology contribute to operation conditions which reduce resolution of different cell populations as shown by FIGS. 5*a*, 6*a*, and 7*a* as compared to shorter flow path utilized by the invention which contributes to operation conditions which increase resolution of different cell populations as shown by FIGS. 5*b*, 6*b*, and 7*b*.

With respect to some embodiments of the invention, a reduced length cell fluid stream (27) can be achieved by shortening the total length of the cell source conduit (28) between the cell source (1) and the injection point (30) until maximum increased resolution is achieved. The distance between the cell source (1) and the injection point (30) can be made substantially shorter than conventional technology, and as shown in FIGS. 4*c* and 4*d* can be less than four inches in length.

With respect to particular configurations of the flow cytometer invention and in with respect to the type of particle populations being separated the various embodiments of the invention can be used independently and in combination to increase the resolution between populations of particles, cells, or sperm cells. Specifically, with regard to an embodiment of the invention used to separate bovine sperm cells as shown by FIGS. 5*b*, 6*b*, and 7*b*, the one piece nozzle (25) utilizing a shorter flow path from the cell source (1) to the injection point (30), but maintaining the injection point (30) at the same distance from the nozzle orifice (5) dramatically increases resolution between sperm cells bearing an X-chromosome (39) and sperm cells bearing a Y-chromosome (40). However, this example is not intended to limit the use of the adjustable injection point (30) invention when analyzing sperm cells to the location used for resolving populations of bovine sperm cells. With respect to embodiments of the invention in which sperm cells from other species of mammals are being analyzed the injection point may have to be more or less close to the nozzle orifice to increase resolution or to initially resolve a population of sperm cells.

Again referring primarily to FIG. 4, the invention can comprise a reduced areal fluid stream (26) within the nozzle (25). The cross sectional area of the conventional fluid stream within the nozzle (2) with respect to some embodiments of the invention (shown by FIGS. 4a and 4b) can be substantially reduced as shown for example by FIGS. 4c or and 4d). The reduced cross sectional area of the fluid stream (26), which when compared to the conventional technology as shown by FIGS. 4a and 4b (Cytomation SX MoFlo® nozzle) as a measure, can for some embodiments of the invention, be between one fourth and one sixth of the conventional cross sectional fluid stream area (33) or less. Moreover, the length of the conventional nozzle (2) can be substantially shortened as to some embodiments of the invention as shown by both FIGS. 4c and 4d to provide an shorter fluid stream flow path. Specifically, with regard to flow separation of bovine spermatozoa a reduced cross sectional flow stream area of about one fifth of the conventional technology shown by FIG. 4c.

Now referring primarily to FIGS. 5, 6, and 7, an example of the enhanced resolution flow cytometer invention used to differentiate X-chromosome bearing and Y-chromosome bearing bovine nuclei is exemplified.

The enhanced resolution flow cytometer invention was set up using the following conditions:

| | |
|---|---|
| Fluid Stream Pressure: | 50.0 psi |
| Nozzle Orifice: | 70 μm |
| Laser Power: | 150 mW |
| Photomultiplier Tube Volts: | 220/230 V |
| Standard: | Fresh Bull Nuclei |
| Sample: | Equinox Lot #19901 |

However, lower fluid stream pressure of between 30 and 40 psi can be used with substantially the same results and increased fertility of sperm cells.

As can be understood from FIGS. 5, 6, and 7 comparative data was taken using conventional flow cytometer technology (FIGS. 5a, 6a, and 7a) and the high resolution flow cytometer invention (FIGS. 5b, 6b, and 7b) at three different event rates of about 25,000 events per second, about 50,000 to about 60,000 events per second, or about 100,000 to about 110,000 events per second. When a spermatozoa stained with a fluorochrome emits a detectable fluorescent emission, an event is counted. The greater the event rate typically the more difficult it can be to differentiate sperm cells based on the difference in magnitude of the detected fluorescent emission. With respect to all event rates, the mixed populations of X-chromosome bearing and Y-chromosome bearing bovine nuclei were differentiated to a greater extent using the high resolution flow cytometer invention as described herein.

Now referring primarily to FIGS. 8 to 11 which show components of an embodiment of the invention. FIG. 8 shows an embodiment of the interchangeable reduced length particle injector (31) having a keyed stop which mates with the nozzle body (25). The beveled tip (41). As to some embodiments of the invention the particle injector can have a diameter of about 1 to about 2 millimeters and have an internal bore of about 0.2 to about 0.3 millimeters. The beveled tip can intersect the plane perpendicular to the longitudinal axis of the particle injector at about 84 degrees with the terminal end of the bevel having a width of about 0.5 to about 0.7 millimeters. The keyed stop (38) an comprise a flat (42 to make rotational orientation consistent.

FIGS. 9 and 10 shows an embodiment of a inner nozzle body (43) keyed with a flat to slidly accept and position the particle injector (31). The inner nozzle body (43) inserts into the outer nozzle body (44) shown by FIG. 10. The outer nozzle body further includes at least one (two in the embodiment of the invention shown by FIG. 10) flow path from the fluid source (45) and can be configured for compression fittings or leak proof fittings to join the fluid source conduit to the outer nozzle body (44).

Figure 11A:
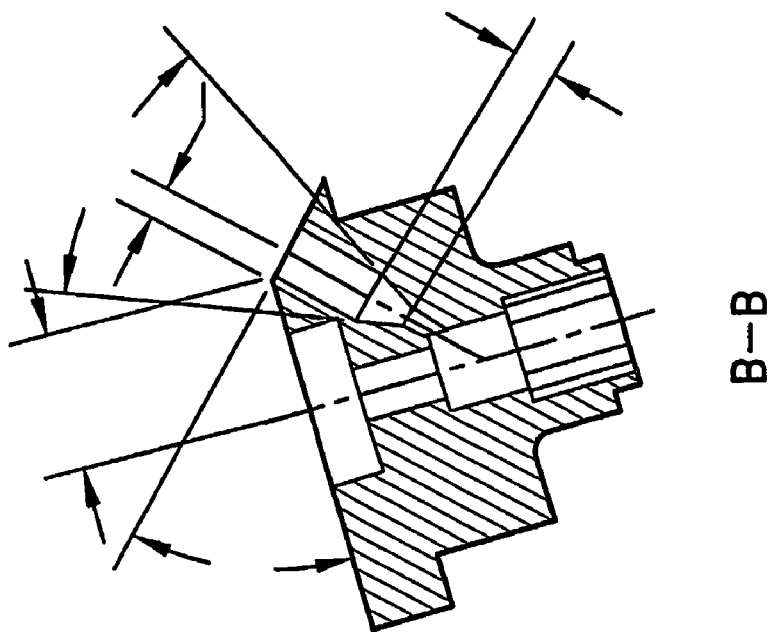
Figure 11B:
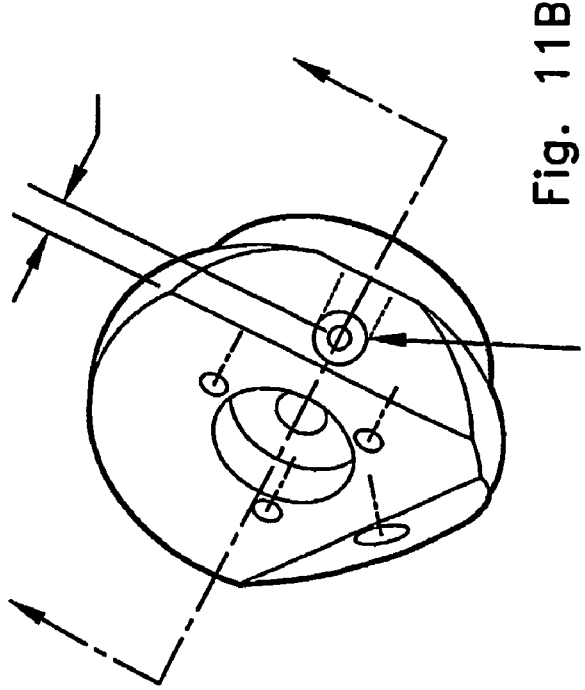

FIG. 11 provides additional FIG. 11a which shows a cross section B-B through the outer nozzle body (44) showing a particular configuration of the sheath fluid path and additional FIG. 11b providing an perspective view of the outer nozzle body.

As can be understood from FIGS. 4c, 4d, 9 and 11, the single piece nozzle (25) engages the outer nozzle body (44) and can be held in place with retaining ring (45). The nozzle assembly invention can be used to replace the conventional nozzle technology shown by FIGS. 1, 2, 4a, and 4b to provide increased resolution as shown by FIGS. 6b, 7b, and 8b.

With respect to asymmetric particle types such as sperm cells the nozzle assembly invention can provide greater orientation of the asymmetric particles within the nozzle body which provides greater consistency in analysis, especially when analysis comprises determination of the amount of emitted fluorescent light or cell volume.

Additionally, the increased resolution can be achieved at very high event rates between 20,000 and 100,000 events per second depending on the type of particle, cell, or sperm cell being analyzed. As a result, a much higher number of sperm may be separated, sorted, collected or recovered each second. This approach yields more product per unit time, and reduces production costs per unit, as the cost of flow cytometer or cell sorter can be a large part of the overall cost of producing separated particles.

When nozzle assembly invention operates with a lower pressure fluid stream, separated or sorted sperm cells collected, even at sort rates greater than 1000 sorts per second can have increased motility, viability, and fertility (sperm cell fertility characteristics) and can as to some species of sperm cell have substantially the same sperm cell fertility characteristics as freshly collected sperm cells in semen.

Because of the increased resolution that can be achieved with the nozzle body assembly, purity of sorted particles can also be increased even at sort rates which are greater than those achieved with the conventional nozzle technology.

The instant nozzle assembly invention generates fewer events in which a partial or full occlusion of the particle injector ( ) occurs. As such, there is less time in which a typical flow cytometer or cell sorter cannot be operated.

The nozzle assembly invention allows, in the event of an occlusion in the injection tube, a rapid removal of the injection tube, without the need to disassemble or dismount the entire nozzle assembly. The injection tube may then be easily inspected, cleaned, and reinstalled, which results in much shorter periods of downtime for such cleaning events, and therefore results in more productive use of the sorting instrument.

The nozzle assembly invention also allows cleaning of the injection tube by an unskilled (or semi-skilled) operator, without the need for a technical repairman. This means the labor costs for the rectification of a partial or full injection tube occlusion event may be reduced. It also means that the operator may immediately rectify such an event without spending time searching for an appropriate repair person.

The nozzle assembly invention allows an operator to observe a loss in separation resolution and rectify it immediately. Using a conventional nozzle assembly, a partial occlusion may not create stoppage of the instrument, but as the occlusion builds, may result in a situation where the resolution function of the instrument is slowly lost, over many hours, days, or even weeks, and during the entire time in which a poorly resolving nozzle is operating, the instrument will typically produce a much lower purity product, or particularly may need to be run at much lower sorting rates, resulting in lesser amounts of product being produced (lower productivity). In practice, the lower productivity is often only noticed by the operator when a skilled technician changes or cleans the nozzle, and the immediate improvement is seen.

The ease of replacement of the injection tube can allow the injection tube to be an item which is used one time only, or for a very limited period of time. In certain uses of the flow cytometer, such as sorting materials such as human fetal cells, or human sperm cells, or human bone marrow cells, where complex and lengthy CIP (clean in place) protocols are needed to assure the elimination of cross contamination between samples, it is convenient and expedient if the CIP procedures may be substituted by replacement of all parts which come in contact with the sample, thereby requiring the replacement of the sample injection tube.

The shorter injection tube, and accompanying smaller nozzle of the instant invention prevent certain types of malformations of the tube such as bending during inspection or assembly, and allow the tube less freedom of motion (vibration) within the nozzle. This maintains the tip of the injection tube closer to the desired injection point within the nozzle, and reduces the number and amplitude of harmonic resonances of the tube within the specific nozzle geometry.

The linear shape of the injection tube in the instant invention allows the injection tube to be inserted more or less deeply into the nozzle, which allows a user to modulate the exact distance between the point in which the sample is injected into the fluid stream and the point of the orifice of the nozzle. By allowing the observation of resolution data to influence the decision on the positioning of the injection tube in the nozzle (feedback control loop), it is possible to establish an injection point location which may change dynamically as other aspects of the instrument operation or sample are changed.

Most nozzle assemblies are expensive components, which are often manufactured in small numbers, and by manufacturers who are not able to create perfectly identical subcomponents. Thus, in practice, each nozzle assembly must be carefully tested, and if not accurate may need to be rebuilt or even discarded. The instant invention simplifies many of the parts of the nozzle assembly, which facilitates a more reliable manufacturing process for various sub-components of the nozzle assembly, and which allows easy replacement of the injection tube which is one of the more common causes of a poorly functioning nozzle. All of this leads to lower manufacturing costs, and more effective use of parts, which in turn lead to reduction in the costs of maintaining one or more production instruments which are used in a 24 hour per day, 7 day per week (24/7) production setting.

The invention can further include an mammalian embryo or a mammal produced using spermatozoa isolated or treated using any of the embodiments of the invention, or can include a mammalian embryo or a mammal of predetermined sex produced using separated spermatozoa in accordance with the various embodiments of the invention, or can include a mammalian embryo or a mammal produced using a sperm cell insemination sample(s) prepared according to the invention having an enriched population of either X-chromosome bearing sperm cells or enriched population of Y-chromosome bearing sperm cells, or a mammalian embryo or a mammal produced in accordance with any embodiment of the invention in which a sperm cell insemination sample containing a low number of sperm cells compared to the typical number used to inseminate that particular species of mammal is used.

As can be easily understood from the foregoing, the basic concepts of the present invention may be embodied in a variety of ways. It involves high resolution sperm cell processing system(s) with certain embodiments configured to provide a high or enhanced flow cytometer system that can be used with a variety of particles, cells, or sperm cells including both techniques as well as devices to accomplish high resolution particle differentiation and separation into enriched populations based upon selected particle characteristics.

In this application, various sperm cell processing techniques are disclosed as part of the results shown to be achieved by the various devices described and as steps that are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this provisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for the full patent application. It should be understood that such language changes and broad claiming will be accomplished when the applicant later (filed by the required deadline) seeks a patent filing based on this provisional filing. The subsequently filed, full patent application will seek examination of as broad a base of claims as deemed within the applicant's right and will be designed to yield a patent covering numerous aspects of the invention both independently and as an overall system.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "flow-sorter" should be understood to encompass disclosure of the act of "flow-sorting"—whether explicitly discussed or not—and, conversely, were there effectively disclosure of the act of "flow-sorting", such a disclosure should be understood to encompass disclosure of a "flow-sorter" and even a "means for flow-sorting" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the sperm cell processing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, and xi) each potentially dependent claim or concept as a dependency on each and every one of the independent claims or concepts presented. In this regard it should be understood that for practical reasons and so as to avoid adding potentially hundreds of claims, the applicant may eventually present claims with initial dependencies only. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

I claim:

1. A method of flow cytometry, comprising the steps of:
   a. obtaining sperm cells of a mammal;
   b. injecting said sperm cells at an injection point along the central longitudinal axis of a fluid stream within a nozzle of a flow cytometer;
   c. forming a plurality of droplets in said fluid stream;
   d. entraining in each of a portion of said plurality of droplets one of said sperm cells injected into said fluid stream;
   e. analyzing said sperm cells entrained in said portion of said plurality of droplets;
   f. discriminating between said sperm cells to generate two populations based upon at least one sperm cell characteristic; and
   g. adjustably varying axial location of said injection point of said sperm cells along said central longitudinal axis in said fluid stream within said nozzle of said flow cytometer to increase resolution of said at least two populations of said sperm cells based upon said at least one sperm cell characteristic.

2. A method of flow cytometry as described in claim 1, wherein said mammal is selected from the group consisting of a bovine mammal, an equine mammal, a ovine mammal, a canine mammal, a feline mammal, a swine mammal, a marine mammal, and a deer mammal.

3. A method of flow cytometry as described in claim 1, wherein said fluid stream comprises a sheath fluid.

4. A method of flow cytometry as described in claim 3, wherein said sheath fluid comprises a sheath fluid having a buffer selected from the group consisting of a citrate buffer, a phosphate buffer, and a HEPES buffer.

5. A method of flow cytometry as described in claim 1, wherein said step of obtaining sperm cells of a mammal comprises the step of obtaining sperm cells of a first species of mammal and obtaining sperm cells of a second species of mammal and wherein said step of adjustably varying axial location of said injection point of said sperm cells along said central longitudinal axis in said fluid stream to increase resolution of said at least two populations of said sperm cells comprises the step of establishing a first injection point for said sperm cells of said first species of mammal at a first location along said central longitudinal axis in said fluid stream to increase resolution of said at least two populations of sperm cells and the step of establishing a second injection point for said sperm cells of said second species of mammal at a second location along said central longitudinal axis in said fluid stream to increase resolution of said at least two populations of sperm cells.

6. A method of flow cytometry as described in claim 1, wherein said step of adjustably varying axial location of said injection point of said sperm cells along said central longitudinal axis in said fluid stream to increase resolution of said at least two populations of said sperm cells comprises the step of adjustably varying axial location at which a particle injector introduces said sperm cells in said fluid stream.

7. A method of flow cytometry as described in claim 6, wherein said step of adjustably varying axial location at which a particle injector introduces said sperm cell in said fluid stream further comprises the step of providing an axially slidly adjustable coupling between said particle injector and a nozzle body.

8. A method of flow cytometry as described in claim 6, wherein said step of adjustably varying axial location at which a particle injector introduces said sperm cell in said fluid stream further comprises the step of operating a mated pair of spiral threads between said particle injector and a nozzle body.

9. A method of flow cytometry as described in claim 6, wherein said step of adjustably varying axial location at which a particle injector introduces said sperm cells in said fluid stream further comprises the step of replacing said particle injector with a second particle injector to alter distance between said injection point of said sperm cells into said fluid stream and a nozzle orifice through which said fluid stream flows.

10. A method of flow cytometry as described in claim 1, wherein said step of adjustably varying location of said injection point of said sperm cells along said central longitudinal axis in said fluid stream to increase resolution of said at least two populations of said sperm cells further comprises the step of adjustably varying axial distance between said injection point of said sperm cells along the central longitudinal axis in said fluid stream and a nozzle orifice through which said fluid stream flows.

11. A method of flow cytometry as described in claim 1, wherein said fluid stream has fluid stream characteristics and wherein said step of adjustably varying axial location of said injection point of said sperm cells in said fluid stream along said central longitudinal axis to increase resolution of said at least two populations of said sperm cells further comprises the step of adjustably varying axial location of said injection point of said sperm cells in response to said fluid stream characteristics.

12. A method of flow cytometry as described in claim 1, wherein said fluid stream has altered fluid stream characteristics and wherein said step of adjustably varying axial location of said injection point of said sperm cells in said fluid stream along said central longitudinal axis to increase resolution of said at least two populations of said sperm cells further comprises the step of adjustably varying axial location of said injection point of said sperm cells in response to said altered fluid stream characteristics.

13. A method of flow cytometry as described in claim 1, further comprising the step of separating said sperm cells into a first population of sperm cells and a second population of sperm cells.

14. A method of flow cytometry as described in claim 13, wherein said step of discriminating between said sperm cells to generate two populations based upon at least one sperm cell characteristic further comprises the step of discriminating between said sperm cells based upon a sex characteristic, and wherein said first population of sperm cells bear an X-chromosome and said second population of sperm cells bear a Y-chromosome.

15. A method of flow cytometry as described in claim 6 wherein said step of adjustably varying axial location at which a particle injector introduces said sperm cell in said fluid stream further comprises the step of adjustably varying axial location of said particle injector with a keyed stop mated with a nozzle body.

* * * * *